US008558040B2

(12) United States Patent
Creazzo et al.

(10) Patent No.: US 8,558,040 B2
(45) Date of Patent: Oct. 15, 2013

(54) METHODS FOR MAKING FOAMS USING BLOWING AGENTS COMPRISING UNSATURATED FLUOROCARBONS

(75) Inventors: Joseph Anthony Creazzo, Wilmington, DE (US); Mario Joseph Nappa, Newark, DE (US); Allen Capron Sievert, Elkton, MD (US); Ekaterina N. Swearingen, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 1725 days.

(21) Appl. No.: 11/591,349

(22) Filed: Nov. 1, 2006

(65) Prior Publication Data

US 2007/0100009 A1 May 3, 2007

Related U.S. Application Data

(60) Provisional application No. 60/732,771, filed on Nov. 1, 2005.

(51) Int. Cl.
*C07C 21/18* (2006.01)
(52) U.S. Cl.
USPC .......................................................... 570/136
(58) Field of Classification Search
None
See application file for complete search history.

(56) References Cited

U.S. PATENT DOCUMENTS

| 3,085,918 | A | 4/1963 | Skerliker et al. |
| 3,723,318 | A | 3/1973 | Butler |
| 3,884,828 | A | 5/1975 | Butler |
| 4,085,073 | A | 4/1978 | Suh et al. |
| 4,394,491 | A | 7/1983 | Hoffman |
| 4,613,708 | A | 9/1986 | Riess et al. |
| 4,704,410 | A | 11/1987 | Booth et al. |
| 4,704,411 | A | 11/1987 | Gansow et al. |
| 5,037,572 | A | 8/1991 | Merchant |
| 5,164,419 | A | 11/1992 | Bartlett et al. |
| 5,204,159 | A | 4/1993 | Tan |
| 5,332,761 | A | 7/1994 | Paquet et al. |
| 5,463,150 | A | 10/1995 | Lui et al. |
| 5,578,137 | A | 11/1996 | Shealy |
| 5,900,185 | A | 5/1999 | Tapscott |
| 5,908,822 | A | 6/1999 | Dishart |
| 5,977,271 | A | 11/1999 | McKay et al. |
| 6,071,580 | A | 6/2000 | Bland et al. |
| 6,590,005 | B2 | 7/2003 | Singh et al. |
| 6,610,250 | B1 | 8/2003 | Tuma |
| 6,703,431 | B2 | 3/2004 | Dietzen et al. |
| 6,787,580 | B2 | 9/2004 | Chonde et al. |
| 2004/0119047 | A1* | 6/2004 | Singh et al. ........... 252/71 |
| 2004/0256594 | A1 | 12/2004 | Singh et al. |
| 2005/0233934 | A1 | 10/2005 | Singh et al. |
| 2007/0077488 | A1 | 4/2007 | Chen et al. |
| 2007/0096051 | A1 | 5/2007 | Nappa et al. |
| 2007/0098646 | A1 | 5/2007 | Nappa et al. |
| 2007/0100009 | A1 | 5/2007 | Creazzo et al. |
| 2007/0100010 | A1 | 5/2007 | Creazzo et al. |
| 2007/0100011 | A1 | 5/2007 | Creazzo et al. |
| 2007/0102021 | A1 | 5/2007 | Nappa et al. |
| 2007/0105738 | A1 | 5/2007 | Nappa et al. |
| 2007/0108403 | A1 | 5/2007 | Sievert et al. |
| 2007/0203046 | A1 | 8/2007 | Minor et al. |
| 2008/0269532 | A1 | 10/2008 | Swearingen |

FOREIGN PATENT DOCUMENTS

| DE | 2534315 | | 2/1976 |
| EP | 0350316 | A1 | 1/1990 |
| EP | 0558763 | A1 | 8/1993 |
| EP | 0 398 147 | B1 | 11/1994 |
| EP | 0731162 | A | 9/1996 |
| GB | 950876 | | 2/1964 |
| JP | 5179043 | A | 7/1993 |
| JP | 5179043 | A | 12/2004 |
| WO | 9423008 | A | 10/1994 |
| WO | 2004037913 | A2 | 5/2004 |
| WO | 2005/099718 | A1 | 10/2005 |
| WO | 2006/101882 | A2 | 6/2006 |
| WO | 2008/134061 | A2 | 11/2008 |
| WO | 2008/154612 | A1 | 12/2008 |
| WO | 2009/014965 | A1 | 1/2009 |
| WO | 2009/014966 | A1 | 1/2009 |
| WO | 2009/032983 | A1 | 3/2009 |
| WO | 2009/073487 | A1 | 6/2009 |
| WO | 2009/085857 | A2 | 7/2009 |

OTHER PUBLICATIONS

Jeanneaux, at al. In Journal of Fluorine Chemistry, vol. 4 (1974), pp. 261-270.
World Meteorological Organization Global Ozone Research and Monitoring Project, Scientific Assessment of Ozone Depletion: 2002, "Source Gases" Report No. 47, Published Mar. 2003, pp. 1.28-1.31.
Gao et al., "Dip-Coating of Ultra-Thin Liquid Lubricant and Its Control for Thin-Film Magnetic Hard Disks", IEEE Transactions on Magnetics, vol. 31, No. 6, 1995, pp. 2982-2984.
Skochdopole, R. E., et al., "Polystyrene Foams", Encyclopedia of Polymer Science, vol. 16 (1989) pp. 193-206.
Santini G. et al.: "The Reaction of Perfluoroalkylcopper Compounds With 1-Bromo-Perfluoroalkyethylenes" Tetrahedron, vol. 29, 1973, pp. 2411-2414 XP002427778 Talbe 3; Compound 2A 2B.
Devallezbernard et al: "Solubility of Respiratory Gases in the 1, 2-Bis(F-Alkyl) Ethenes" Journal De Chimie Physique, Societe de Chimie Physique, Paris, FR, vol. 85, No. 10, pp. 947-952, XP008077143.
Le Blanc M et al: "A Strategy for the Synthesis of Pure, Inert Perfluoroalkylated Derivatives Designed for Flood Substitution" Oxyen Carrying Colloidal Blood Substitutes. International Symposium Perfluorochem. Blood Substitutes, 1982, pp. 43-49, XPOO8077176.

(Continued)

*Primary Examiner* — Yevegeny Valenrod

(57) ABSTRACT

Disclosed herein are blowing agents comprising fluorocarbons and/or hydrofluorocarbons useful in foamable compositions. Also disclosed are methods for forming a foam comprising the aforementioned blowing agents.

14 Claims, No Drawings

(56) References Cited

OTHER PUBLICATIONS

Pedler A. E. et al : "The Synthesis and Dehydrofluorination of Some Polyfluoroalkanes" J. Fluorine Chem., vol. 1 No. 3, 1972, pp. 337-345, XP002427764.

H. Boden et. al., Chapter 4, Polyurethane Handbook, Edited by G. Oertel, Hanser Publishers, NY 1985.

H. Grunbauer et. al., "Fine Celled CFC-Free RIGID Roam—New Machinery With Low Boiling Blowing Agents"Published in Polyurethanes 92 From the Proceeding of the SPI 34th Annual Technical/Marketing Conference, Oct. 21-24, 1993, New Orleans, Louisiana.

M. Taverna et. al., "Soluble or Insoluble Alternative Blowing Agents? processing technologies for Both Alternatives, Presented by Equipment Manufacturer", Published in Polyurethanes World Congress 1991 From the Proceedings of the SPI/SOPA Sep. 24-26, 1991, Acropolis, Nice, France.

Devallezbernard et. al., "Solubility of Respiratory Gases in the 1, 2-Bis(F-Alkyl) Ethenes", Journal De Chimie Physique, Societe de Chimie Physique, Paris, France, vol. 85, No. 10, 1988, pp. 947-952, XP008077143.

\* cited by examiner

# METHODS FOR MAKING FOAMS USING BLOWING AGENTS COMPRISING UNSATURATED FLUOROCARBONS

CROSS REFERENCE TO RELATED APPLICATION(S)

This application claims the benefit of priority of U.S. Provisional Application 60/732,771, filed Nov. 1, 2005, and incorporated herein by reference, and is further related to co-filed and jointly owned application titled Blowing Agents for Forming Foam Comprising Unsaturated Fluorocarbons, Ser. No. 11/591,350 and further related to co-filed and jointly owned application also titled Blowing Agents for Forming Foam Comprising Unsaturated Fluorocarbons Ser. No. 11/391,400, both of which are also incorporated herein by reference.

FIELD OF THE INVENTION

The disclosure herein relates to blowing agent compositions comprising unsaturated fluorocarbons and/or unsaturated hydrofluorocarbons. The disclosure herein further relates to the use of the blowing agent compositions in the process for manufacturing plastic foams.

BACKGROUND OF THE INVENTION

Closed-cell polyisocyanate-based foams are widely used for insulation purposes, for example, in building construction and in the manufacture of energy efficient electrical appliances. In the construction industry, polyurethane (polyisocyanurate) board stock is used in roofing and siding for its insulation and load-carrying capabilities. Poured and sprayed polyurethane foams are widely used for a variety of applications including insulating roofs, insulating large structures such as storage tanks, insulating appliances such as refrigerators and freezers, insulating refrigerated trucks and railcars, etc.

All of these various types of polyurethane foams require blowing (expansion) agents for their manufacture. Insulating foams depend on the use of halocarbon blowing agents, not only to foam the polymer, but primarily for their low vapor thermal conductivity, a very important characteristic for insulation value. Historically, polyurethane foams used CFCs (chlorofluorocarbons, for example CFC-11, trichlorofluoromethane) and HCFCs (hydrochlorofluorocarbons, for example HCFC-141b, 1,1-dichloro-1-fluoroethane) as the primary blowing agent. However, due to the implication of chlorine-containing molecules such as the CFCs and HCFCs in the destruction of stratospheric ozone, the production and use of CFCs and HCFCs has been restricted by the Montreal Protocol. More recently, hydrofluorocarbons (HFCs), which do not contribute to the destruction of stratospheric ozone, have been employed as blowing agents for polyurethane foams. An example of an HFC employed in this application is HFC-245fa (1,1,1,3,3-pentafluoropropane).

A second type of insulating foam is thermoplastic foam, primarily polystyrene foam. Polyolefin foams (polystyrene, polyethylene, and polypropylene) are widely used in insulation and packaging applications. These thermoplastic foams were generally made with CFC-12 (dichlorodifluoromethane) as the blowing agent. More recently HCFCs (HCFC-22, chlorodifluoromethane) or blends of HCFCs (HCFC-22/HCFC-142b) or HFCs (HFC-152a) have been employed as blowing agents for polystyrene.

A third important type of insulating foam is phenolic foam. These foams, which have very attractive flammability characteristics, were generally made with CFC-11 (trichlorofluoromethane) and CFC-113 (1,1,2-trichloro-1,2,2-trifluoroethane) blowing agents In addition to closed-cell foams, open-cell foams are also of commercial interest, for example in the production of fluid-absorbent articles. U.S. Pat. No. 6,703,431 (Dietzen, et. al.) describes open-cell foams based on thermoplastics polymers that are useful for fluid-absorbent hygiene articles such as wound contact materials. U.S. Pat. No. 6,071,580 (Bland, et. al.) describes absorbent extruded thermoplastic foams which can be employed in various absorbency applications. Open-cell foams have also found application in evacuated or vacuum panel technologies, for example in the production of evacuated insulation panels as described in U.S. Pat. No. 5,977,271 (Malone). Using open-cell foams in evacuated insulation panels, it has been possible to obtain R values of 10 to 15 per inch of thickness depending upon the evacuation or vacuum level, polymer type, cell size, density, and open cell content of the foam. These open-cell foams have traditionally been produced employing CFCs, HCFCs, or more recently, HFCs as blowing agents.

Multimodal foams are also of commercial interest, and are described, for example, in U.S. Pat. No. 6,787,580 (Chonde, et. al.) and U.S. Pat. No. 5,332,761 (Paquet, et. al.). A multimodal foam is a foam having a multimodal cell size distribution, and such foams have particular utility in thermally insulating articles since they often have higher insulating values (R-values) than analogous foams having a generally uniform cell size distribution. These foams have been produced employing CFCs, HCFCs, and, more recently, HFCs as the blowing agent.

As discussed above, the production of various types of foams historically employed CFCs as the blowing agent. In general, the CFCs produce foams exhibiting good thermal insulation, low flammability and excellent dimensional stability. However, despite these advantages the CFCs have fallen into disfavor due to their implication in the destruction of stratospheric ozone, as well as their implication in contributing to global warming.

HCFCs have been proposed as CFC substitutes, and are currently employed as foam blowing agents. However, the HCFCs have also been shown to contribute to the depletion of stratospheric ozone, and as a result their use has come under scrutiny, and the widespread use of HCFCs is scheduled for eventual phase out under the Montreal Protocol.

More recently HFCs have been proposed and employed as foam blowing agents. The HFCs do not contribute to the destruction of stratospheric ozone, but are of concern due to their contribution to the "greenhouse effect", i.e., they contribute to global warming. As a result of their contribution to global warming, the HFCs have come under scrutiny, and their widespread use may also be limited in the future.

Hydrocarbons have also been proposed as foam blowing agents. However, these compounds are flammable, and many are photochemically reactive, and as a result contribute to the production of ground level ozone (i.e., smog). Such compounds are typically referred to as volatile organic compounds (VOCs), and are subject to environmental regulations.

There is need for producing foams that provide low flammability, good thermal insulation and high dimensional stability by using a blowing agent that has substantially no ozone depletion potential (ODP) and no or very low global warming potential (GWP).

There is also need to provide a process for producing plastic foams employing a blowing agent which has significantly less photochemical reactivity than the hydrocarbons, and hence does not contribute to the formation of ambient ozone and ground level smog.

SUMMARY OF THE INVENTION

One aspect is for a blowing agent comprising at least one fluorocarbon or hydrofluorocarbon selected from the group consisting of:

(i) a hydrofluorocarbon having the formula E- or Z-$R^1CH=CHR^2$, wherein $R^1$ and $R^2$ are, independently, $C_1$ to $C_6$ perfluoroalkyl groups; and (ii) a fluorocarbon or hydrofluorocarbon selected from the group consisting of $CF_3CF=CHF$, $CF_3CH=CF_2$, $CHF_2CF=CF_2$, $CHF_2CH=CHF$, $CF_3CF=CH_2$, $CF_3CH=CHF$, $CH_2FCF=CF_2$, $CHF_2CH=CF_2$, $CHF_2CF=CHF$, $CHF_2CF=CH_2$, $CF_3CH=CH_2$, $CH_3CF=CF_2$, $CH_2FCHCF_2$, $CH_2FCF=CHF$, $CHF_2CH=CHF$, $CF_3CF=CFCF_3$, $CF3CF_2CF=CF_2$, $CF_3CF=CHCF_3$, $CF_3CF_2CF=CH_2$, $CF_3CH=CHCF_3$, $CF_3CF_2CH=CH_2$, $CF_2=CHCF_2CF_3$, $CF_2=CFCHFCF_3$, $CF_2=CFCF_2CHF_2$, $CHF_2CH=CHCF_3$, $(CF_3)_2C=CHCF_3$, $CF_3CF=CHCF_2CF_3$, $CF_3CH=CFCF_2CF_3$, $(CF_3)_2CFCH=CH_2$, $CF_3CF_2CF_2CH=CH_2$, $CF_3(CF_2)_3CF=CF_2$, $CF_3CF_2CF=CFCF_2CF_3$, $(CF_3)_2C=C(CF_3)_2$, $(CF_3)_2CFCF=CHCF_3$, $CF_2=CFCF_2CH_2F$, $CF_2=CFCHFCHF_2$, $CH_2=C(CF_3)_2$, $CH_2CF_2CF=CF_2$, $CH_2FCF=CFCHF_2$, $CH_2FCF_2CF=CF_2$, $CF_2=C(CF_3)(CH_3)$, $CH_2=C(CHF_2)(CF_3)$, $CH_2=CHCF_2CHF_2$, $CF_2=C(CHF_2)(CH_3)$, $CHF=C(CF_3)(CH_3)$, $CH_2=C(CHF_2)_2$, $CF_3CF=CFCH_3$, $CH_3CF=CHCF_3$, $CF_2=CFCF_2CF_3$, $CHF=CFCF_2CF_3$, $CF_2=CHCF_2CF_3$, $CF_2=CFCF_2CHF_2$, $CHF_2CF=CFCF_3$, $CF_3CF=CFCF_2CHF_2$, $CF_3CF=CFCHFCF_3$, $CHF=CFCF(CF_3)_2$, $CF_2=CFCH(CF_3)_2$, $CF_3CH=C(CF_3)_2$, $CF_2=CHCF(CF_3)_2$, $CH_2=CFCF_2CF_2CF_3$, $CHF=CFCF_2CF_2CHF_2$, $CH_2=C(CF_3)CF_2CF_3$, $CF_2=CHCH(CF_3)_2$, $CHF=CHCF(CF_3)_2$, $CF_2=C(CF_3)CH_2CF_3$, $CH_2=CFCF_2CH_2CF_3$, $CH_2=CFCH_2CF_3$, $CF_3CF=C(CF_3)(CH_3)$, $CH_2=CFCH(CF_3)_2$, $CHF=CHCH(CF_3)_2$, $CH_2FCH=C(CF_3)_2$, $CH_3CF=C(CF_3)_2$, $CH_2=CHCF_2CHFCF_3$, $CH_2C(CF_3)CH_2CF_3$, $(CF_3)_2C=CHC_2F_5$, $(CF_3)_2CFCF=CHCF_3$, $CH_2=CHC(CF_3)_3$, $(CF_3)_2C=C(CH_3)(CF_3)$, $CH_2=CFCF_2CH(CF_3)_2$, $CF_3CF=C(CH_3)CF_2CF_3$, $CF_3CH=CHCH(CF_3)_2$, $CH_2=CHCF_2CF_2CHF_2$, $(CF_3)_2C=CHCF_2CH_3$, $CH_2=C(CF_3)CH_2C_2F_5$, $CH_2=CHCH_2CF_2C_2F_5$, $CH_2=CHCH_2CF_2C_2F_5$, $CF_3CF_2CF=CFC_2H_5$, $CH_2=CHCH_2CF(CF_3)_2$, $CF_3CF=CHCH(CF_3)(CH_3)$, $(CF_3)_2C=CFC_2H5$, cyclo-$CF_2CF_2CF_2CH=CH-$, cyclo-$CF_2CF_2CH=CH-$, $CF_3CF_2CF_2C(CH_3)=CH_2$, $CF_3CF_2CF_2CH=CHCH_3$, cyclo-$CF_2CF_2CF=CF-$, cyclo-$CF_2CF=CFCF_2CF_2-$, cyclo-$CF_2CF=CFCF_2CF_2CF_2$, $CF_3CF_2CF_2CF_2CH=CH_2$, $CF_3CH=CHCF_2CF_3$, $CF_3CF_2CH=CHCF_2CF_3$, $CF_3CH=CHCF_2CF_3$, $CF_3CF=CFC_2F_5$, $CF_3CF=CFCF_2C_2F_5$, $CF_3CF=CFCF_2C_2F_5$, $CF_3CH=CFCF_2C_2F_5$, $CF_3CF=CHCF_2C_2F_5$, $CF_3CF_2CH=CFCF_2C_2F_5$, $CF_3CF_2CF=CHCF_2C_2F_5$, $C_2F_5CF_2CF=CHCH_3$, $C_2F_5CF=CHCH_3$, $(CF_3)_2C=CHCH_3$, $CF_3C(CH_3)=CHCF_3$, $CHF=CFC_2F_5$, $CHF_2CF=CFCF_3$, $(CF_3)_2C=CHF$, $CH_2FCF=CFCF_3$, $CHF=CHCF_2CF_3$, $CHF_2CH=CFCF_3$, $CHF=CFCHFCF_3$, $CF_3CH=CFCHF_2$, $CHF=CFCF_2CHF_2$, $CHF_2CF=CFCHF_2$, $CH_2CF=CFCF_3$, $CH_2FCH=CFCF_3$, $CH_2=CFCHFCF_3$, $CH_2=CFCF_2CHF_2$, $CF_3CH=CFCH_2F$, $CHF=CFCH_2CF_3$, $CHF=CHCHFCF_3$, $CHF=CHCF_2CHF_2$, $CHF_2CF=CHCHF_2$, $CHF=CFCHFCHF_2$, $CF_3CF=CHCH_3$, $CF_2=CHCF_2Br$, $CHF=CBrCHF_2$, $CHBr=CHCF_3$, $CF_3CBr=CFCF_3$, $CH_2=CBrCF_2CF_3$, $CHBr=CHCF_2CF_3$, $CH_2=CHCF_2CF_2Br$, $CH_2=CHCBrFCF_3$, $CH_3CBr=CHCF_3$, $CF_3CBr=CHCH_3$, $(CF_3)_2C=CHBr$, $CF_3CF=CBrCF_2CF_3$, E-$CHF_2CBr=CFC_2F_5$, Z-$CHF_2CBr=CFC_2F_5$, $CF_2=CBrCHFC_2F_5$, $(CF_3)_2CFCBr=CH_2$, $CHBr=CF(CF_2)_2CHF_2$, $CH_2=CBrCF_2C_2F_5$, $CF_2=C(CH_2Br)CF_3$, $CH_2=C(CBrF_2)CF_3$, $(CF_3)_2CHCH=CHBr$, $(CF_3)_2C=CHCH_2Br$, $CH_2=CHCF(CF_3)CBrF_2$, $CF_2=CHCF_2CH_2CBrF_2$, $CFBr=CHCF_3$, $CFBr=CFCF_3$, $CF_3CF_2CF_2CBr=CH_2$, and $CF_3(CF_2)_3CBr=CH_2$.

Another aspect is for a closed cell foam prepared by foaming a foamable composition in the presence of a blowing agent described above.

A further aspect is for a foamable composition comprising a polyol and a blowing agent described above.

Another aspect is for a foam premix composition comprising a polyol and a blowing agent described above.

Additionally, one aspect is for a method of forming a foam comprising:

(a) adding to a foamable composition a blowing agent described above; and (b) reacting the foamable composition under conditions effective to form a foam.

A further aspect is for a method of forming a polyisocyanate based foam comprising reacting at least one organic polyisocyanate with at least one active hydrogen-containing compound in the presence of a blowing agent described above.

Another aspect is for a polyisocyanate foam produced by said method.

Other objects and advantages will become apparent to those skilled in the art upon reference to the detailed description that hereinafter follows.

DETAILED DESCRIPTION OF THE INVENTION

Applicants specifically incorporate the entire content of all cited references in this disclosure. Applicants also incorporate by reference the co-owned and concurrently filed applications entitled "Solvent Compositions Comprising Unsaturated Fluorinated Hydrocarbons" ( U.S. Application No. 60/732,771), "Blowing Agents for Forming Foam Comprising Unsaturated Fluorocarbons" (U.S. Application No. 60/732,090), "Aerosol Propellants Comprising Unsaturated Fluorocarbons" (U.S. Application No. 60/732,791), and "Compositions Comprising Fluoroolefins and Uses Thereof" (U.S. Application No. 60/732,581). Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

One aspect provides blowing agents having the formula E- or Z—$R^1CH=CHR^2$ (Formula I), wherein $R^1$ and $R^2$ are, independently, $C_1$ to $C_6$ perfluoroalkyl groups. Examples of $R^1$ and $R^2$ groups include, but are not limited to, $CF_3$, $C_2F_5$, $CF_2CF_2CF_3$, $CF(CF_3)_2$, $CF_2CF_2CF_2CF_3$, $CF(CF_3)CF_2CF_3$, $CF_2CF(CF_3)_2$, $C(CF_3)_3$, $CF_2CF_2CF_2CF_2CF_3$, $CF_2CF_2CF(CF_3)_2$, $C(CF_3)_2C_2F_5$, $CF_2CF_2CF_2CF_2CF_2CF_3$, $CF(CF_3)CF_2CF_2C_2F_5$, and $C(CF_3)_2CF_2C_2F_5$. Exemplary, non-limiting Formula I compounds are presented in Table 1.

TABLE 1

| Code | Structure | Chemical Name |
|---|---|---|
| F11E | $CF_3CH=CHCF_3$ | 1,1,1,4,4,4-hexafluorobut-2-ene |
| F12E | $CF_3CH=CHC_2F_5$ | 1,1,1,4,4,5,5,5-octafluoropent-2-ene |
| F13E | $CF_3CH=CHCF_2C_2F_5$ | 1,1,1,4,4,5,5,6,6,6-decafluorohex-2-ene |
| F13iE | $CF_3CH=CHCF(CF_3)_2$ | 1,1,1,4,5,5,5-heptafluoro-4-(trifluoromethyl)pent-2-ene |
| F22E | $C_2F_5CH=CHC_2F_5$ | 1,1,1,2,2,5,5,6,6,6-decafluorohex-3-ene |
| F14E | $CF_3CH=CH(CF_2)_3CF_3$ | 1,1,1,4,4,5,5,6,6,7,7,7-dodecafluorohept-2-ene |
| F14iE | $CF_3CH=CHCF_2CF—(CF_3)_2$ | 1,1,1,4,4,5,6,6,6-nonafluoro-5-(trifluoromethyl)hex-2-ene |
| F14sE | $CF_3CH=CHCF(CF_3)—C_2F_5$ | 1,1,1,4,5,5,6,6,6-nonafluoro-4-(trifluoromethyl)hex-2-ene |
| F14tE | $CF_3CH=CHC(CF_3)_3$ | 1,1,1,5,5,5-hexafluoro-4,4-bis(trifluoromethyl)pent-2-ene |
| F23E | $C_2F_5CH=CHCF_2C_2F_5$ | 1,1,1,2,2,5,5,6,6,7,7,7-dodecafluorohept-3-ene |
| F23iE | $C_2F_5CH=CHCF(CF_3)_2$ | 1,1,1,2,2,5,6,6,6-nonafluoro-5-(trifluoromethyl)hex-3-ene |
| F15E | $CF_3CH=CH(CF_2)_4CF_3$ | 1,1,1,4,4,5,5,6,6,7,7,8,8,8-tetradecafluorooct-2-ene |
| F15iE | $CF_3CH=CH—CF_2CF_2CF(CF_3)_2$ | 1,1,1,4,4,5,5,6,7,7,7-undecafluoro-6-(trifluoromethyl)hept-2-ene |
| F15tE | $CF_3CH=CH—C(CF_3)_2C_2F_5$ | 1,1,1,5,5,6,6,6-octafluoro-4,4-bis(trifluoromethyl)hex-2-ene |
| F24E | $C_2F_5CH=CH(CF_2)_3CF_3$ | 1,1,1,2,2,5,5,6,6,7,7,8,8,8-tetradecafluorooct-3-ene |
| F24iE | $C_2F_5CH=CHCF_2CF—(CF_3)_2$ | 1,1,1,2,2,5,5,6,7,7,7-undecafluoro-6-(trifluoromethyl)hept-3-ene |
| F24sE | $C_2F_5CH=CHCF(CF_3)—C_2F_5$ | 1,1,1,2,2,5,6,6,7,7,7-undecafluoro-5-(trifluoromethyl)hept-3-ene |
| F24tE | $C_2F_5CH=CHC(CF_3)_3$ | 1,1,1,2,2,6,6,6-octafluoro-5,5-bis(trifluoromethyl)hex-3-ene |
| F33E | $C_2F_5CF_2CH=CH—CF_2C_2F_5$ | 1,1,1,2,2,3,3,6,6,7,7,8,8,8-tetradecafluorooct-4-ene |
| F3i3iE | $(CF_3)_2CFCH=CH—CF(CF_3)_2$ | 1,1,1,2,5,6,6,6-octafluoro-2,5-bis(trifluoromethyl)hex-3-ene |
| F33iE | $C_2F_5CF_2CH=CH—CF(CF_3)_2$ | 1,1,1,2,5,5,6,6,7,7,7-undecafluoro-2-(trifluoromethyl)hept-3-ene |
| F16E | $CF_3CH=CH(CF_2)_5CF_3$ | 1,1,1,4,4,5,5,6,6,7,7,8,8,,9,9,9-hexadecafluoronon-2-ene |
| F16sE | $CF_3CH=CHCF(CF_3)—(CF_2)_2C_2F_5$ | 1,1,1,4,5,5,6,6,7,7,8,8,8-tridecafluoro-4-(trifluoromethyl)hept-2-ene |
| F16tE | $CF_3CH=CHC(CF_3)_2—CF_2C_2F_5$ | 1,1,1,6,6,6-octafluoro-4,4-bis(trifluoromethyl)hept-2-ene |
| F25E | $C_2F_5CH=CH(CF_2)_4CF_3$ | 1,1,1,2,2,5,5,6,6,7,7,8,8,9,9,9-hexadecafluoronon-3-ene |
| F25iE | $C_2F_5CH=CH—CF_2CF_2CF(CF_3)_2$ | 1,1,1,2,2,5,5,6,6,7,8,8,8-tridecafluoro-7-(trifluoromethyl)oct-3-ene |
| F25tE | $C_2F_5CH=CH—C(CF_3)_2C_2F_5$ | 1,1,1,2,2,6,6,7,7,7-decafluoro-5,5-bis(trifluoromethyl)hept-3-ene |
| F34E | $C_2F_5CF_2CH=CH—(CF_2)_3CF_3$ | 1,1,1,2,2,3,3,6,6,7,7,8,8,9,9,9-hexadecafluoronon-4-ene |
| F34iE | $C_2F_5CF_2CH=CH—CF_2CF(CF_3)_2$ | 1,1,1,2,2,3,3,6,7,7,8,8,8-tridecafluoro-7-(trifluoromethyl)oct-4-ene |
| F34sE | $C_2F_5CF_2CH=CH—CF(CF_3)C_2F_5$ | 1,1,1,2,2,3,3,6,7,7,8,8,8-tridecafluoro-6-(trifluoromethyl)oct-4-ene |
| F34tE | $C_2F_5CF_2CH=CH—C(CF_3)_3$ | 1,1,1,5,5,6,6,7,7,7-decafluoro-2,2-bis(trifluoromethyl)hept-3-ene |
| F3i4E | $(CF_3)_2CFCH=CH—(CF_2)_3CF_3$ | 1,1,1,2,5,5,6,6,7,7,8,8,8-tridecafluoro-2(trifluoromethyl)oct-3-ene |
| F3i4iE | $(CF_3)_2CFCH=CH—CF_2CF(CF_3)_2$ | 1,1,1,2,5,5,6,7,7,7-decafluoro-2,6-bis(trifluoromethyl)hept-3-ene |
| F3i4sE | $(CF_3)_2CFCH=CH—CF(CF_3)C_2F_5$ | 1,1,1,2,5,6,6,7,7,7-decafluoro-2,5-bis(trifluoromethyl)hept-3-ene |
| F3i4tE | $(CF_3)_2CFCH=CH—C(CF_3)_3$ | 1,1,1,2,6,6,6-heptafluoro-2,5,5-tris(trifluoromethyl)hex-3-ene |
| F26E | $C_2F_5CH=CH(CF_2)_5CF_3$ | 1,1,1,2,2,5,5,6,6,7,7,8,8,9,9,10,10,10-octadecafluorodec-3-ene |
| F26sE | $C_2F_5CH=CHCF(CF_3)—(CF_2)_2C_2F_5$ | 1,1,1,2,2,5,6,6,7,7,8,8,9,9,9-pentadecafluoro-5-(trifluoromethyl)non-3-ene |
| F26tE | $C_2F_5CH=CHC(CF_3)_2—CF_2C_2F_5$ | 1,1,1,2,2,6,6,7,7,8,8,8-dodecafluoro-5,5-bis(trifluoromethyl)oct-3-ene |
| F35E | $C_2F_5CF_2CH=CH—(CF_2)_4CF_3$ | 1,1,1,2,2,3,3,6,6,7,7,8,8,9,9,10,10,10-octadecafluorodec-4-ene |
| F35iE | $C_2F_5CF_2CH=CH—CF_2CF_2CF(CF_3)_2$ | 1,1,1,2,2,3,3,6,6,7,7,8,8,9,9,9-pentadecafluoro-8-(trifluoromethyl)non-4-ene |
| F35tE | $C_2F_5CF_2CH=CH—C(CF_3)_2C_2F_5$ | 1,1,1,2,2,3,3,7,7,8,8,8-dodecafluoro-6,6-bis(trifluoromethyl)oct-4-ene |
| F3i5E | $(CF_3)_2CFCH=CH—(CF_2)_4CF_3$ | 1,1,1,2,5,5,6,6,7,7,8,8,9,9,9-pentadecafluoro-2-(trifluoromethyl)non-3-ene |
| F3i5iE | $(CF_3)_2CFCH=CH—CF_2CF_2CF(CF_3)_2$ | 1,1,1,2,5,5,6,6,7,8,8,8-dodecafluoro-2,7-bis(trifluoromethyl)oct-3-ene |

TABLE 1-continued

| Code | Structure | Chemical Name |
|---|---|---|
| F3i5tE | $(CF_3)_2CFCH=CH-C(CF_3)_2C_2F_5$ | 1,1,1,2,6,6,7,7,7-nonafluoro-2,5,5-tris(trifluoromethyl)hept-3-ene |
| F44E | $CF_3(CF_2)_3CH=CH-(CF_2)_3CF_3$ | 1,1,1,2,2,3,3,4,4,7,7,8,8,9,9,10,10,10-octadecafluorodec-5-ene |
| F44iE | $CF_3(CF_2)_3CH=CH-CF_2CF(CF_3)_2$ | 1,1,1,2,3,3,6,6,7,7,8,8,9,9,9-pentadecafluoro-2-(trifluoromethyl)non-4-ene |
| F44sE | $CF_3(CF_2)_3CH=CH-CF(CF_3)C_2F_5$ | 1,1,1,2,2,3,6,6,7,7,8,8,9,9,9-pentadecafluoro-3-(trifluoromethyl)non-4-ene |
| F44tE | $CF_3(CF_2)_3CH=CH-C(CF_3)_3$ | 1,1,1,5,5,6,6,7,7,8,8,8-dodecafluoro-2,2,-bis(trifluoromethyl)oct-3-ene |
| F4i4iE | $(CF_3)_2CFCF_2CH=CH-CF_2CF(CF_3)_2$ | 1,1,1,2,3,3,6,6,7,8,8,8-dodecafluoro-2,7-bis(trifluoromethyl)oct-4-ene |
| F4i4sE | $(CF_3)_2CFCF_2CH=CH-CF(CF_3)C_2F_5$ | 1,1,1,2,3,3,6,7,7,8,8,8-dodecafluoro-2,6-bis(trifluoromethyl)oct-4-ene |
| F4i4tE | $(CF_3)_2CFCF_2CH=CH-C(CF_3)_3$ | 1,1,1,5,5,6,7,7,7-nonafluoro-2,2,6-tris(trifluoromethyl)hept-3-ene |
| F4s4sE | $C_2F_5CF(CF_3)CH=CH-CF(CF_3)C_2F_5$ | 1,1,1,2,2,3,6,7,7,8,8,8-dodecafluoro-3,6-bis(trifluoromethyl)oct-4-ene |
| F4s4tE | $C_2F_5CF(CF_3)CH=CH-C(CF_3)_3$ | 1,1,1,5,6,6,7,7,7-nonafluoro-2,2,5-tris(trifluoromethyl)hept-3-ene |
| F4t4tE | $(CF_3)_3CCH=CH-C(CF_3)_3$ | 1,1,1,6,6,6-hexafluoro-2,2,5,5-tetrakis(trifluoromethyl)hex-3-ene |

Compounds of Formula I may be prepared by contacting a perfluoroalkyl iodide of the formula $R^1I$ with a perfluoroalkyltrihydroolefin of the formula $R^2CH=CH_2$ to form a trihydroiodoperfluoroalkane of the formula $R^1CH_2CHIR^2$. This trihydroiodoperfluoroalkane can then be dehydroiodinated to form $R^1CH=CHR^2$. Alternatively, the olefin $R^1CH=CHR^2$ may be prepared by dehydroiodination of a trihydroiodoperfluoroalkane of the formula $R^1CHICH_2R^2$ formed in turn by reacting a perfluoroalkyl iodide of the formula $R^2I$ with a perfluoroalkyltrihydroolefin of the formula $R^1CH=CH_2$.

Said contacting of a perfluoroalkyl iodide with a perfluoroalkyltrihydroolefin may take place in batch mode by combining the reactants in a suitable reaction vessel capable of operating under the autogenous pressure of the reactants and products at reaction temperature. Suitable reaction vessels include those fabricated from stainless steels, in particular of the austenitic type, and the well-known high nickel alloys such as Monel® nickel-copper alloys, Hastelloy® nickel based alloys and Inconel® nickel-chromium alloys.

Alternatively, the reaction may be conducted in semi-batch mode in which the perfluoroalkyltrihydroolefin reactant is added to the perfluoroalkyl iodide reactant by means of a suitable addition apparatus such as a pump at the reaction temperature.

The ratio of perfluoroalkyl iodide to perfluoroalkyltrihydroolefin should be between about 1:1 to about 4:1, preferably from about 1.5:1 to 2.5:1. Ratios less than 1.5:1 tend to result in large amounts of the 2:1 adduct as reported by Jeanneaux, et al. in Journal of Fluorine Chemistry, Vol. 4, pages 261-270 (1974).

Preferred temperatures for contacting of said perfluoroalkyl iodide with said perfluoroalkyltrihydroolefin are preferably within the range of about 150° C. to 300° C., preferably from about 170° C. to about 250° C., and most preferably from about 180° C. to about 230° C.

Suitable contact times for the reaction of the perfluoroalkyl iodide with the perfluoroalkyltrihydroolefin are from about 0.5 hour to 18 hours, preferably from about 4 to about 12 hours.

The trihydroiodoperfluoroalkane prepared by reaction of the perfluoroalkyl iodide with the perfluoroalkyltrihydroolefin may be used directly in the dehydroiodination step or may preferably be recovered and purified by distilled prior to the dehydroiodination step.

The dehydroiodination step is carried out by contacting the trihydroiodoperfluoroalkane with a basic substance. Suitable basic substances include alkali metal hydroxides (e.g., sodium hydroxide or potassium hydroxide), alkali metal oxide (for example, sodium oxide), alkaline earth metal hydroxides (e.g., calcium hydroxide), alkaline earth metal oxides (e.g., calcium oxide), alkali metal alkoxides (e.g., sodium methoxide or sodium ethoxide), aqueous ammonia, sodium amide, or mixtures of basic substances such as soda lime. Preferred basic substances are sodium hydroxide and potassium hydroxide.

Said contacting of the trihydroiodoperfluoroalkane with a basic substance may take place in the liquid phase preferably in the presence of a solvent capable of dissolving at least a portion of both reactants. Solvents suitable for the dehydroiodination step include one or more polar organic solvents such as alcohols (e.g., methanol, ethanol, n-propanol, isopropanol, n-butanol, isobutanol, and tertiary butanol), nitriles (e.g., acetonitrile, propionitrile, butyronitrile, benzonitrile, or adiponitrile), dimethyl sulfoxide, N,N-dimethylformamide, N,N-dimethylacetamide, or sulfolane. The choice of solvent may depend on the boiling point of the product and the ease of separation of traces of the solvent from the product during purification. Typically, ethanol or isopropanol are good solvents for the reaction.

Typically, the dehydroiodination reaction may be carried out by addition of one of the reactants (either the basic substance or the trihydroiodoperfluoroalkane) to the other reactant in a suitable reaction vessel. Said reaction vessel may be fabricated from glass, ceramic, or metal and is preferably agitated with an impellor or stirring mechanism.

Temperatures suitable for the dehydroiodination reaction are from about 10° C. to about 100° C., preferably from about 20° C. to about 70° C. The dehydroiodination reaction may be carried out at ambient pressure or at reduced or elevated pressure. Of note are dehydroiodination reactions in which the compound of Formula I is distilled out of the reaction vessel as it is formed.

Alternatively, the dehydroiodination reaction may be conducted by contacting an aqueous solution of said basic substance with a solution of the trihydroiodoperfluoroalkane in one or more organic solvents of lower polarity such as an alkane (e.g., hexane, heptane, or octane), aromatic hydrocarbon (e.g., toluene), halogenated hydrocarbon (e.g., methylene chloride, ethylene dichloride, chloroform, carbon tetrachloride, or perchloroethylene), or ether (e.g., diethyl ether, methyl tert-butyl ether, tetrahydrofuran, 2-methyl tetrahydrofuran, dioxane, dimethoxyethane, diglyme, or tetraglyme) in the presence of a phase transfer catalyst. Suitable phase transfer catalysts include quaternary ammonium halides (e.g., tetrabutylammonium bromide, tetrabutylammonium hydrosulfate, triethylbenzylammonium chloride, dodecyltrimethylammonium chloride, and tricaprylylmethylammonium chloride), quaternary phosphonium halides (e.g., triphenylmethylphosphonium bromide and tetraphenylphosphonium chloride), and cyclic ether compounds known in the art as crown ethers (e.g., 18-crown-6 and 15-crown-5).

Alternatively, the dehydroiodination reaction may be conducted in the absence of solvent by adding the trihydroiodoperfluoroalkane to a solid or liquid basic substance.

Suitable reaction times for the dehydroiodination reactions are from about 15 minutes to about six hours or more depending on the solubility of the reactants. Typically the dehydroiodination reaction is rapid and requires about 30 minutes to about three hours for completion.

The compound of formula I may be recovered from the dehydroiodination reaction mixture by phase separation after addition of water, by distillation, or by a combination thereof.

The compositions disclosed herein may comprise a single compound of Formula I, for example, one of the compounds in Table 1, or may comprise a combination of compounds of Formula I.

In addition to the inventive compounds described above, compounds presented in Table 2 can be used as blowing agents.

TABLE 2

| Name | Structure | Chemical name |
|---|---|---|
| HFC-1225s | $C_3HF_5$ | |
| HFC-1225ye | $CF_3CF=CHF$ | 1,2,3,3,3-pentafluoro-1-propene |
| HFC-1225zc | $CF_3CH=CF_2$ | 1,1,3,3,3-pentafluoro-1-propene |
| HFC-1225yc | $CHF_2CF=CF_2$ | 1,1,2,3,3-pentafluoro-1-propene |
| HFC-1234s | $C_3H_2F_4$ | |
| HFC-1234ye | $CHF_2CF=CHF$ | 1,2,3,3-tetrafluoro-1-propene |
| HFC-1234yf | $CF_3CF=CH_2$ | 2,3,3,3-tetrafluoro-1-propene |
| HFC-1234ze | $CF_3CH=CHF$ | 1,3,3,3-tetrafluoro-1-propene |
| HFC-1234yc | $CH_2FCF=CF_2$ | 1,1,2,3-tetrafluoro-1-propene |
| HFC-1234zc | $CHF_2CH=CF_2$ | 1,1,3,3-tetrafluoro-1-propene |
| HFC-1234ye | $CHF_2CF=CHF$ | 1,2,3,3-tetrafluoro-1-propene |
| HFC-1243s | $C_3H_3F_3$ | |
| HFC-1243yf | $CHF_2CF=CH_2$ | 2,3,3-trifluoro-1-propene |
| HFC-1243zf | $CF_3CH=CH_2$ | 3,3,3-trifluoro-1-propene |
| HFC-1243yc | $CH_3CF=CF_2$ | 1,1,2-trifluoro-1-propene |
| HFC-1243zc | $CH_2FCH=CF_2$ | 1,1,3-trifluoro-1-propene |
| HFC-1243ye | $CHF_2CF=CHF$ | 1,2,3-trifluoro-1-propene |
| HFC-1243ze | $CHF_2CH=CHF$ | 1,3,3-trifluoro-1-propene |
| FC-1318s | $C_4F_8$ | |
| FC-1318my | $CF_3CF=CFCF_3$ | 1,1,1,2,3,4,4,4-octafluoro-2-butene |
| FC-1318cy | $CF_3CF_2CF=CF_2$ | 1,1,2,3,3,4,4,4-octafluoro-1-butene |
| HFC-1327s | $C_4HF_7$ | |
| HFC-1327my | $CF_3CF=CHCF_3$ | 1,1,1,2,4,4,4-heptafluoro-2-butene |
| HFC-1327ye | $CHF=CFCF_2CF_3$ | 1,2,3,3,4,4,4-heptafluoro-1-butene |
| HFC-1327py | $CHF_2CF=CFCF_3$ | 1,1,1,2,3,4,4-heptafluoro-2-butene |
| HFC-1327et | $(CF_3)_2C=CHF$ | 1,3,3,3-tetrafluoro-2-(trifluoromethyl)-1-propene |
| HFC-1327cz | $CF_2=CHCF_2CF_3$ | 1,1,3,3,4,4,4-heptafluoro-1-butene |
| HFC-1327cye | $CF_2=CFCHFCF_3$ | 1,1,2,3,4,4,4-heptafluoro-1-butene |
| HFC-1327cyc | $CF_2=CFCF_2CHF_2$ | 1,1,2,3,3,4,4-heptafluoro-1-butene |
| HFC-1336s | $C_4H_2F_6$ | |
| HFC-1336yf | $CF_3CF_2CF=CH_2$ | 2,3,3,4,4,4-hexafluoro-1-butene |
| HFC-1336ze | $CHF=CHCF_2CF_3$ | 1,3,3,4,4,4-hexafluoro-1-butene |
| HFC-1336eye | $CHF=CFCHFCF_3$ | 1,2,3,4,4,4-hexafluoro-1-butene |
| HFC-1336eyc | $CHF=CFCF_2CHF_2$ | 1,2,3,3,4,4-hexafluoro-1-butene |
| HFC-1336pyy | $CHF_2CF=CFCHF_2$ | 1,1,2,3,4,4-hexafluoro-2-butene |
| HFC-1336qy | $CH_2FCF=CFCF_3$ | 1,1,1,2,3,4-hexafluoro-2-butene |
| HFC-1336pz | $CHF_2CH=CFCF_3$ | 1,1,1,2,4,4-hexafluoro-2-butene |
| HFC-1336mzy | $CF_3CH=CFCHF_2$ | 1,1,1,3,4,4-hexafluoro-2-butene |
| HFC-1336qc | $CF_2=CFCF_2CH_2F$ | 1,1,2,3,3,4-hexafluoro-1-butene |
| HFC-1336pe | $CF_2=CFCHFCHF_2$ | 1,1,2,3,4,4-hexafluoro-1-butene |
| HFC-1336ft | $CH_2=C(CF_3)_2$ | 3,3,3-trifluoro-2-(trifluoromethyl)-1-propene |
| HFC-1345s | $C_4H_3F_5$ | |
| HFC-1345qz | $CH_2FCH=CFCF_3$ | 1,1,1,2,4-pentafluoro-2-butene |
| HFC-1345mzy | $CF_3CH=CFCH_2F$ | 1,1,1,3,4-pentafluoro-2-butene |
| HFC-1345fz | $CF_3CF_2CH=CH_2$ | 3,3,4,4,4-pentafluoro-1-butene |
| HFC-1345mzz | $CHF_2CH=CHCF_3$ | 1,1,1,4-pentafluoro-2-butene |
| HFC-1345sy | $CH_3CF=CFCF_3$ | 1,1,1,2,3-pentafluoro-2-butene |
| HFC-1345fyc | $CH_2=CFCF_2CHF_2$ | 2,3,3,4,4-pentafluoro-1-butene |
| HFC-1345pyz | $CHF_2CF=CHCHF_2$ | 1,1,2,4,4-pentafluoro-2-butene |
| HFC-1345cyc | $CH_3CF_2CF=CF_2$ | 1,1,2,3,3-pentafluoro-1-propene |
| HFC-1345pyy | $CH_2FCF=CFCHF_2$ | 1,1,2,3,4-pentafluoro-2-butene |
| HFC-1345eyc | $CH_2FCF_2CF=CF_2$ | 1,2,3,3,4-pentafluoro-1-butene |
| HFC-1345ctm | $CF_2=C(CF_3)(CH_3)$ | 1,1,3,3,3-pentafluoro-2-methyl-1-propene |
| HFC-1345ftp | $CH_2=C(CHF_2)(CF_3)$ | 2-(difluoromethyl)-3,3,3-trifluoro-1-propene |

TABLE 2-continued

| Name | Structure | Chemical name |
|---|---|---|
| HFC-1354s | $C_4H_4F_4$ | |
| HFC-1354fzc | $CH_2\!=\!CHCF_2CHF_2$ | 3,3,4,4-tetrafluoro-1-butene |
| HFC-1354ctp | $CF_2\!=\!C(CHF_2)(CH_3)$ | 1,1,3,3-tetrafluoro-2-methyl-1-propene |
| HFC-1354etm | $CHF\!=\!C(CF_3)(CH_3)$ | 1,3,3,3-tetrafluoro-2-methyl-1-propene |
| HFC-1354tfp | $CH_2\!=\!C(CHF_2)_2$ | 2-(difluoromethyl)-3,3-difluoro-1-propene |
| HFC-1354my | $CF_3CF\!=\!CFCH_3$ | 1,1,1,2-tetrafluoro-2-butene |
| HFC-1354mzy | $CH_3CF\!=\!CHCF_3$ | 1,1,1,3-tetrafluoro-2-butene |
| FC-141-10s | $C_5F_{10}$ | |
| FC-141-10myy | $CF_3CF\!=\!CFCF_2CF_3$ | 1,1,1,2,3,4,4,5,5,5-decafluoro-2-pentene |
| FC-141-10cy | $CF_2\!=\!CFCF_2CF_2CF_3$ | 1,1,2,3,3,4,4,5,5,5-decafluoro-1-pentene |
| HFC-1429s | $C_5HF_9$ | |
| HFC-1429mzt | $(CF_3)_2C\!=\!CHCF_3$ | 1,1,1,4,4,4-hexafluoro-2-(trifluoromethyl)-2-butene |
| HFC-1429myz | $CF_3CF\!=\!CHCF_2CF_3$ | 1,1,1,2,4,4,5,5,5-nonafluoro-2-pentene |
| HFC-1429mzy | $CF_3CH\!=\!CFCF_2CF_3$ | 1,1,1,3,4,4,5,5,5-nonafluoro-2-pentene |
| HFC-1429eyc | $CHF\!=\!CFCF_2CF_2CF_3$ | 1,2,3,3,4,4,5,5,5-nonafluoro-1-pentene |
| HFC-1429czc | $CF_2\!=\!CHCF_2CF_2CF_3$ | 1,1,3,3,4,4,5,5,5-nonafluoro-1-pentene |
| HFC-1429cycc | $CF_2\!=\!CFCF_2CF_2CHF_2$ | 1,1,2,3,3,4,4,5,5-nonafluoro-1-pentene |
| HFC-1429pyy | $CHF_2CF\!=\!CFCF_2CF_3$ | 1,1,2,3,4,4,5,5,5-nonafluoro-2-pentene |
| HFC-1429myyc | $CF_3CF\!=\!CFCF_2CHF_2$ | 1,1,1,2,3,4,4,5,5-nonafluoro-2-pentene |
| HFC-1429myye | $CF_3CF\!=\!CFCHFCF_3$ | 1,1,1,2,3,4,5,5,5-nonafluoro-2-pentene |
| HFC-1429eyym | $CHF\!=\!CFCF(CF_3)_2$ | 1,2,3,4,4,4-hexafluoro-3-(trifluoromethyl)-1-butene |
| HFC-1429cyzm | $CF_2\!=\!CFCH(CF_3)_2$ | 1,1,2,4,4,4-hexafluoro-3-(trifluoromethyl)-1-butene |
| HFC-1429mzt | $CF_3CH\!=\!C(CF_3)_2$ | 1,1,1,4,4,4-hexafluoro-3-(trifluoromethyl)-2-butene |
| HFC-1429czym | $CF_2\!=\!CHCF(CF_3)_2$ | 1,1,3,4,4,4-hexafluoro-3-(trifluoromethyl)-1-butene |
| HFC-1438s | $C_5H_2F_8$ | |
| HFC-1438fy | $CH_2\!=\!CFCF_2CF_2CF_3$ | 2,3,3,4,4,5,5,5-octafluoro-1-pentene |
| HFC-1438eycc | $CHF\!=\!CFCF_2CF_2CHF_2$ | 1,2,3,3,4,4,5,5-octafluoro-1-pentene |
| HFC-1438ftmc | $CH_2\!=\!C(CF_3)CF_2CF_3$ | 3,3,4,4,4-pentafluoro-2-(trifluoromethyl)-1-butene |
| HFC-1438czzm | $CF_2\!=\!CHCH(CF_3)_2$ | 1,1,4,4,4-pentafluoro-3-(trifluoromethyl)-1-butene |
| HFC-1438ezym | $CHF\!=\!CHCF(CF_3)_2$ | 1,3,4,4,4-pentafluoro-3-(trifluoromethyl)-1-butene |
| HFC-1438ctmf | $CF_2\!=\!C(CF_3)CH_2CF_3$ | 1,1,4,4,4-pentafluoro-2-(trifluoromethyl)-1-butene |
| HFC-1447s | $C_5H_3F_7$ | |
| HFC-1447fzy | $(CF_3)_2CFCH\!=\!CH_2$ | 3,4,4,4-tetrafluoro-3-(trifluoromethyl)-1-butene |
| HFC-1447fz | $CF_3CF_2CF_2CH\!=\!CH_2$ | 3,3,4,4,5,5,5-heptafluoro-1-pentene |
| HFC-1447fycc | $CH_2\!=\!CFCF_2CF_2CHF_2$ | 2,3,3,4,4,5,5-heptafluoro-1-pentene |
| HFC-1447czcf | $CF_2\!=\!CHCF_2CH_2CF_3$ | 1,1,3,3,5,5,5-heptafluoro-1-pentene |
| HFC-1447mytm | $CF_3CF\!=\!C(CF_3)(CH_3)$ | 1,1,1,2,4,4,4-heptafluoro-3-methyl-2-butene |
| HFC-1447fyz | $CH_2\!=\!CFCH(CF_3)_2$ | 2,4,4,4-tetrafluoro-3-(trifluoromethyl)-1-butene |
| HFC-1447ezz | $CHF\!=\!CHCH(CF_3)_2$ | 1,4,4,4-tetrafluoro-3-(trifluoromethyl)-1-butene |
| HFC-1447qzt | $CH_2FCH\!=\!C(CF_3)_2$ | 1,4,4,4-tetrafluoro-3-(trifluoromethyl)-2-butene |
| HFC-1447syt | $CH_3CF\!=\!C(CF_3)_2$ | 2,4,4,4-tetrafluoro-3-(trifluoromethyl)-2-butene |
| HFC-1456s | $C_5H_4F_6$ | |
| HFC-1456szt | $(CF_3)_2C\!=\!CHCH_3$ | 3-(trifluoromethyl)-4,4,4-trifluoro-2-butene |
| HFC-1456szy | $CF_3CF_2CF\!=\!CHCH_3$ | 3,4,4,5,5,5-hexafluoro-2-pentene |
| HFC-1456mstz | $CF_3C(CH_3)\!=\!CHCF_3$ | 1,1,1,4,4,4-hexafluoro-2-methyl-2-butene |
| HFC-1456fzce | $CH_2\!=\!CHCF_2CHFCF_3$ | 3,3,4,5,5,5-hexafluoro-1-pentene |

TABLE 2-continued

| Name | Structure | Chemical name |
|---|---|---|
| HFC-1456ftmf | $CH_2=C(CF_3)CH_2CF_3$ | 4,4,4-trifluoro-2-(trifluoromethyl)-1-butene |
| FC-151-12s | $C_6F_{12}$ | |
| FC-151-12c | $CF_3(CF_2)_3CF=CF_2$ | 1,1,2,3,3,4,4,5,5,6,6,6-dodecafluoro-1-hexene (or perfluoro-1-hexene) |
| FC-151-12mcy | $CF_3CF_2CF=CFCF_2CF_3$ | 1,1,1,2,2,3,4,5,5,6,6,6-dodecafluoro-3-hexene (or perfluoro-3-hexene) |
| FC-151-12mmtt | $(CF_3)_2C=C(CF_3)_2$ | 1,1,1,4,4,4-hexafluoro-2,3-bis(trifluoromethyl)-2-butene |
| FC-151-12mmzz | $(CF_3)_2CFCF=CFCF_3$ | 1,1,1,2,3,4,5,5,5-nonafluoro-4-(trifluoromethyl)-2-pentene |
| HFC-152-11s | $C_6HF_{11}$ | |
| HFC-152-11mmtz | $(CF_3)_2C=CHC_2F_5$ | 1,1,1,4,4,5,5,5-octafluoro-2-(trifluoromethyl)-2-pentene |
| HFC-152-11mmyyz | $(CF_3)_2CFCF=CHCF_3$ | 1,1,1,3,4,5,5,5-octafluoro-4-(trifluoromethyl)-2-pentene |
| HFC-1549s | $C_6H_3F_9$ | |
| PFBE (or HFC-1549fz) | $CF_3CF_2CF_2CF_2CH=CH_2$ | 3,3,4,4,5,5,6,6,6-nonafluoro-1-hexene (or perfluorobutylethylene) |
| HFC-1549fztmm | $CH_2=CHC(CF_3)_3$ | 4,4,4-trifluoro-3,3-bis(trifluoromethyl)-1-butene |
| HFC-1549mmtts | $(CF_3)_2C=C(CH_3)(CF_3)$ | 1,1,1,4,4,4-hexafluoro-3-methyl-2-(trifluoromethyl)-2-butene |
| HFC-1549fycz | $CH_2=CFCF_2CH(CF_3)_2$ | 2,3,3,5,5,5-hexafluoro-4-(trifluoromethyl)-1-pentene |
| HFC-1549myts | $CF_3CF=C(CH_3)CF_2CF_3$ | 1,1,1,2,4,4,5,5,5-nonafluoro-3-methyl-2-pentene |
| HFC-1549mzzz | $CF_3CH=CHCH(CF_3)_2$ | 1,1,1,5,5,5-hexafluoro-4-(trifluoromethyl)-2-pentene |
| HFC-1558s | $C_6H_4F_8$ | |
| HFC-1558szy | $CF_3CF_2CF_2CF=CHCH_3$ | 3,4,4,5,5,6,6,6-octafluoro-2-hexene |
| HFC-1558fzccc | $CH_2=CHCF_2CF_2CF_2CHF_2$ | 3,3,4,4,5,5,6,6-octafluoro-2-hexene |
| HFC-1558mmtzc | $(CF_3)_2C=CHCF_2CH_3$ | 1,1,1,4,4-pentafluoro-2-(trifluoromethyl)-2-pentene |
| HFC-1558ftmf | $CH_2=C(CF_3)CH_2C_2F_5$ | 4,4,5,5,5-pentafluoro-2-(trifluoromethyl)-1-pentene |
| HFC-1567s | $C_6H_5F_7$ | |
| HFC-1567fts | $CF_3CF_2CF_2C(CH_3)=CH_2$ | 3,3,4,4,5,5,5-heptafluoro-2-methyl-1-pentene |
| HFC-1567szz | $CF_3CF_2CF_2CH=CHCH_3$ | 4,4,5,5,6,6,6-heptafluoro-2-hexene |
| HFC-1567fzfc | $CH_2=CHCH_2CF_2C_2F_5$ | 4,4,5,5,6,6,6-heptafluoro-1-hexene |
| HFC-1567sfyy | $CF_3CF_2CF=CFC_2H_5$ | 1,1,1,2,2,3,4-heptafluoro-3-hexene |
| HFC-1567fzfy | $CH_2=CHCH_2CF(CF_3)_2$ | 4,5,5,5-tetrafluoro-4-(trifluoromethyl)-1-pentene |
| HFC-1567myzzm | $CF_3CF=CHCH(CF_3)(CH_3)$ | 1,1,1,2,5,5,5-heptafluoro-4-methyl-2-pentene |
| HFC-1567mmtyf | $(CF_3)_2C=CFC_2H_5$ | 1,1,1,3-tetrafluoro-2-(trifluoromethyl)-2-pentene |
| FC-161-14s | $C_7F_{14}$ | |
| FC-161-14myy | $CF_3CF=CFCF_2CF_2C_2F_5$ | 1,1,1,2,3,4,4,5,5,6,6,7,7,7-tetradecafluoro-2-heptene |
| FC-161-14mcyy | $CF_3CF_2CF=CFCF_2C_2F_5$ | 1,1,1,2,2,3,4,5,5,6,6,7,7,7-tetradecafluoro-2-heptene |
| HFCs-162-13s | $C_7HF_{13}$ | |
| HFC-162-13mzy | $CF_3CH=CFCF_2CF_2C_2F_5$ | 1,1,1,3,4,4,5,5,6,6,7,7,7-tridecafluoro-2-heptene |
| HFC162-13myz | $CF_3CF=CHCF_2CF_2C_2F_5$ | 1,1,1,2,4,4,5,5,6,6,7,7,7-tridecafluoro-2-heptene |
| HFC-162-13mczy | $CF_3CF_2CH=CFCF_2C_2F_5$ | 1,1,1,2,2,4,5,5,6,6,7,7,7-tridecafluoro-3-heptene |
| HFC-162-13mcyz | $CF_3CF_2CF=CHCF_2C_2F_5$ | 1,1,1,2,2,3,5,5,6,6,7,7,7-tridecafluoro-3-heptene |
| Cyclic fluoroolefins | Cyclo[—CX=CY(CXY)$_n$—] | |
| HFC-C1316cc | cyclo-$CF_2CF_2CF=CF$— | 1,2,3,3,4,4-hexafluorocyclobutene |
| HFC-C1334cc | cyclo-$CF_2CF_2CH=CH$— | 3,3,4,4-tetrafluorocyclobutene |
| HFC-C1436 | cyclo-$CF_2CF_2CF_2CH=CH$— | 3,3,4,4,5,5,-hexafluorocyclopentene |
| HFC-C1418y | cyclo-$CF_2CF=CFCF_2CF_2$— | 1,2,3,3,4,4,5,5-octafluorocyclopentene |
| FC-C151-10y | cyclo-$CF_2CF=CFCF_2CF_2CF_2$— | 1,2,3,3,4,4,5,5,6,6-decafluorocyclohexene |

The compounds listed in Table 2 are available commercially or may be prepared by processes known in the art.

In addition to the inventive compounds described above, the bromine-containing fluorocarbons or hydrofluorocarbons presented in Table 3 can be used as blowing agents.

TABLE 3

| Structure | Chemical Names |
|---|---|
| $CF_2=CHCF_2Br$ | 3-bromo-1,1,3,3-tetrafluoropropene |
| $CF_2=CFCBrH_2$ | 3-bromo-1,1,2-trifluoropropene |
| $CHF=CBrCF_3$ | 2-bromo-1,3,3,3-tetrafluoropropene |
| $CHF=CHCBrF_2$ | 3-bromo-1,3,3-trifluoropropene |
| $CHF=CBrCHF_2$ | 2-bromo-1,3,3-trifluoropropene |
| $CHBr=CFCF_3$ | 1-bromo-2,3,3,3-tetrafluoropropene |
| $CHBr=CHCF_3$ | 1-bromo-3,3,3-trifluoropropene |
| $CH_2=CBrCF_3$ | 2-bromo-3,3,3-trifluoropropene |
| $CH_2=CFCBrF_2$ | 3-bromo-2,3,3-trifluoropropene |
| $CFBr=CHCF_3$ | 1-bromo-1,3,3,3-tetrafluoropropene |
| $CFBr=CFCF_3$ | 1-bromopentafluoropropene |
| $CH_2=CBrCF_2CF_3$ | 2-bromo-3,3,4,4,4-pentafluoro-1-butene |
| $CHBr=CHCF_2CF_3$ | 1-bromo-3,3,4,4,4-pentafluoro-1-butene |
| $CH_2=CHCF_2CF_2Br$ | 4-bromo-3,3,4,4-tetrafluoro-1-butene |
| $CH_2=CHCBrFCF_3$ | 3-bromo-3,4,4,4-tetrafluoro-1-butene |
| $CF_3CBr=CFCF_3$ | 2-bromo-1,1,1,3,4,4,4-heptafluoro-2-butene |
| $CH_3CBr=CHCF_3$ | 2-bromo-4,4,4-trifluoro-2-butene |
| $CF_3CBr=CHCH_3$ | 2-bromo-1,1,1-trifluoro-2-butene |
| $(CF_3)_2C=CHBr$ | 1-bromo-3,3,3-trifluoro-2-(trifluoromethyl)-propene |
| $CF_3CF=CBrCF_2CF_3$ | 3-bromo-1,1,1,2,4,4,5,5,5-nonafluoro-2-pentene |
| $E-CHF_2CBr=CFC_2F_5$ | E-2-bromo-1,1,3,4,4,5,5,5-octafluoro-2-pentene |
| $Z-CHF_2CBr=CFC_2F_5$ | Z-2-bromo-1,1,3,4,4,5,5,5-octafluoro-2-pentene |
| $CF_2=CBrCHFC_2F_5$ | 2-bromo-1,1,3,4,4,5,5,5-octafluoro-1-pentene |
| $CHBr=CF(CF_2)_2CHF_2$ | 1-bromo-2,3,3,4,4,5,5-heptafluoro-1-pentene |
| $CH_2=CBrCF_2C_2F_5$ | 2-bromo-3,3,4,4,5,5,5-heptafluoro-1-pentene |
| $CF_2=CHCF_2CH_2CBrF_2$ | 5-bromo-1,1,3,3,5,5-hexafluoro-1-pentene |
| $(CF_3)_2CFCBr=CH_2$ | 2-bromo-3,4,4,4-tetrafluoro-3-(trifluoromethyl)-1-butene |
| $CF_2=C(CH_2Br)CF_3$ | 2-(bromomethyl)-1,1,3,3,3-pentafluoropropene |
| $CH_2=C(CBrF_2)CF_3$ | 2-(bromodifluoromethyl)-3,3,3-trifluoropropene |
| $(CF_3)_2CHCH=CHBr$ | 1-bromo-4,4,4-trifluoro-3-(trifluoromethyl)-1-butene |
| $(CF_3)_2C=CHCH_2Br$ | 4-bromo-1,1,1-trifluoro-2-(trifluoromethyl)-2-butene |
| $CH_2=CHCF(CF_3)CBrF_2$ | 3-(bromodifluoromethyl)-3,4,4,4-tetrafluoro-1-butene |
| $CF_3CF_2CF_2CBr=CH_2$ | 2-bromo-3,3,4,4,5,5,5-heptafluoro-1-pentene |
| $CF_3(CF_2)_3CBr=CH_2$ | 2-bromo-3,3,4,4,5,5,6,6,6-nonafluoro-1-hexene |

The compounds listed in Table 3 are available commercially or may be prepared by processes known in the art.

1-Bromo-3,3,4,4,4-pentafluoro-1-butene may be prepared by a three step sequence beginning with reaction of phosphorous tribromide with 3,3,4,4,4-pentafluoro-1-butanol to give 4-bromo-1,1,1,2,2-pentafluorobutane. Thermal bromination of 4-bromo-1,1,1,2,2-pentafluorobutane at 350-400° C. gives 4,4-dibromo-1,1,1,2,2-pentafluorobutane which may in turn be heated with powdered potassium hydroxide to give the desired bromobutene.

2-Bromo-3,4,4,4-tetrafluoro-3-(trifluoromethyl)-1-butene may be prepared by addition of bromine to 3,4,4-tetrafluoro-3-(trifluoromethyl)-1-butene followed by treatment of the resulting dibromide with ethanolic potassium hydroxide.

Many of the compounds of Formula I, Table 1, Table 2 and Table 3 exist as different configurational isomers or stereoisomers. When the specific isomer is not designated, the present disclosure is intended to include all single configurational isomers, single stereoisomers, or any combination thereof. For instance, $CF_3CH=CHCF_3$ is meant to represent the E-isomer, Z-isomer, or any combination or mixture of both isomers in any ratio. Another example is $C_2F_5CF_2CH=CH-CF_2C_2F_5$, by which is represented the E-isomer, Z-isomer, or any combination or mixture of both isomers in any ratio.

HFC-1225ye may exist as one of two configurational isomers, E or Z. HFC-1225ye as used herein refers to the isomers, E-HFC-1225ye (CAS reg no. 5595-10-8) or Z-HFC-1225ye (CAS reg. no. 5528-43-8), as well as any combinations or mixtures of such isomers.

Blowing agents can comprise a single compound as listed, for example, in Table 2, or may comprise a combination of compounds from Table 2 or, alternatively, a combination of compounds from Table 1, Table 2, Table 3, and/or Formula I.

The amount of the fluorocarbons (FCs) or HFCs contained in the present compositions (from, e.g., Formula I, Table 1, or Table 2, or Table 3) can vary widely, depending the particular application, and compositions containing more than trace amounts and less than 100% of the compound are within broad the scope of the present disclosure.

The compositions disclosed herein may be prepared by any convenient method to combine the desired amounts of the individual components. A preferred method is to weigh the desired component amounts and thereafter combine the components in an appropriate vessel. Agitation may be used, if desired.

Other embodiments provide foamable compositions, and preferably thermoset or thermoplastic foam compositions, prepared using the compositions of the present disclosure. In such foam embodiments, one or more of the present compositions are included as or part of a blowing agent in a foamable composition, which composition preferably includes one or more additional components capable of reacting and/or foaming under the proper conditions to form a foam or cellular structure. Another aspect relates to foam, and preferably closed cell foam, prepared from a polymer foam formulation containing a blowing agent comprising the compositions of the present disclosure.

The present disclosure further relates to a method for replacing or substituting for the blowing agent in a foamable composition having a GWP of about 150 or more, or a high GWP blowing agent, with a composition having a lower GWP. One method comprises providing a composition comprising at least one fluoroolefin of the present invention as the replacement. In another embodiment of the present invention the foamable composition of the present invention, having a lower GWP than the composition being replaced or substituted is used to produce thermoplastic or thermoset foams. Global warming potentials (GWPs) are an index for estimating relative global warming contribution due to atmospheric emission of a kilogram of a particular greenhouse gas compared to emission of a kilogram of carbon dioxide. GWP can be calculated for different time horizons showing the effect of atmospheric lifetime for a given gas. The GWP for the 100 year time horizon is commonly the value referenced.

A high GWP blowing agent would be any compound capable of functioning as a blowing agent having a GWP at the 100 year time horizon of about 1000 or greater, alternatively 500 or greater, 150 or greater, 100 or greater, or 50 or greater. Foam expansion agents that are in need of replacement, based upon GWP calculations published by the Intergovernmental Panel on Climate Change (IPCC), include but are not limited to HFC-134a and HFC-227ea.

The present disclosure will provide compositions that have zero or low ozone depletion potential and low global warming potential (GWP). The fluoroolefins of the present invention or mixtures of fluoroolefins of this invention with other blowing agents or foamable compositions will have global warming potentials that are less than many hydrofluorocarbon blowing agents or foamable compositions currently in use. Typically, the fluoroolefins of the present invention are expected to have GWP of less than about 25. One aspect of the present invention is to provide a blowing agent with a global warming potential of less than 1000, less than 500, less than 150, less than 100, or less than 50. Another aspect of the present invention is to reduce the net GWP of foamable compositions by adding fluoroolefins to said mixtures.

The present invention further relates to a method for lowering the GWP of the methods for manufacturing open, closed and multi-modal foams, said method comprising combining at least one fluoroolefin of the present invention with a resin (for thermoplastic foams) or into a B-side mixture (thermoplastic) to produce a foamable composition with a GWP of lower than 25. The GWP of may be determined that the GWP of a mixture or combination of compounds may be calculated as a weighted average of the GWP for each of the pure compounds.

The present compositions also preferably have an Ozone Depletion Potential (ODP) of not greater than 0.05, more preferably not greater than 0.02 and even more preferably about zero. As used herein, "ODP" is as defined in "The Scientific Assessment of Ozone Depletion, 2002, A report of the World Meteorological Association's Global Ozone Research and Monitoring Project," which is incorporated herein by reference.

Certain embodiments provide foam premixes, foamable compositions, and preferably polyurethane or polyisocyanate foam compositions, and methods of preparing foams. In such foam embodiments, one or more of the compositions of the present disclosure are included as a blowing agent in a foamable composition, which foamable composition preferably includes one or more additional components capable of reacting and/or foaming under the proper conditions to form a foam or cellular structure. Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments.

In certain embodiments, it is often desirable to employ certain other ingredients in preparing foams. Among these additional ingredients are catalysts, surfactants, flame retardants, preservatives, colorants, antioxidants, reinforcing agents, filler, antistatic agents, nucleating agents and the like.

Polyurethane foams are generally prepared by combining and reacting an isocyanate with a polyol in the presence of a blowing or expanding agent and auxiliary chemicals added to control and modify both the polyurethane reaction itself and the properties of the final polymer. For processing convenience, these materials can be premixed into two non-reacting parts typically referred to as the "A-side" and the "B-side".

The term "B-side" is intended to mean polyol or polyol containing mixture. A polyol containing mixture usually includes the polyol, the blowing or expanding agent and auxiliary chemicals, like catalysts, surfactants, stabilizers, chain extenders, cross-linkers, water, fire retardants, smoke suppressants, pigments, coloring materials, fillers, etc.

The term "A-side" is intended to mean isocyanate or isocyanate containing mixture. An isocyanate containing mixture may include the isocyanate, the blowing or expanding agent and auxiliary chemicals, like catalysts, surfactants, stabilizers, chain extenders, cross-linkers, water, fire retardants, smoke suppressants, pigments, coloring materials, fillers, etc.

To prepare the foam, appropriate amounts of A-side and B-side are then combined to react.

When preparing a foam by a process disclosed herein, it is generally preferred to employ a minor amount of a surfactant to stabilize the foaming reaction mixture until it cures. Such surfactants may comprise a liquid or solid organosilicone compound. Other, less preferred surfactants include polyethylene glycol ethers of long chain alcohols, tertiary amine or alkanolamine salts of long chain alkyl acid sulfate esters, alkyl sulfonic esters and alkyl arylsulfonic acids. The surfactants are employed in amounts sufficient to stabilize the foaming reaction mixture against collapse and to prevent the formation of large, uneven cells. About 0.2 to about 5 parts or even more of the surfactant per 100 parts by weight of polyol are usually sufficient.

One or more catalysts for the reaction of the polyol with the polyisocyanate may also be used. Any suitable urethane catalyst may be used, including tertiary amine compounds and organometallic compounds. Such catalysts are used in an amount which measurably increases the rate of reaction of the polyisocyanate. Typical amounts are about 0.1 to about 5 parts of catalyst per 100 parts by weight of polyol.

Useful flame retardants include, for example, tri(2-chloroethyl)phosphate, tri(2-chloropropyl)phosphate, tri(2,3-dibromopropyl)-phosphate, tri(1,3-dichloropropyl) phosphate, diammonium phosphate, various halogenated aromatic compounds, antimony oxide, aluminum trihydrate, polyvinyl chloride, and the like.

The methods of forming a foam generally comprise providing a blowing agent composition of the present disclosure, adding (directly or indirectly) the blowing agent composition to a foamable composition, and reacting the foamable composition under the conditions effective to form a foam or cellular structure. Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments.

Polyisocyanate-based foams are prepared, e.g., by reacting at least one organic polyisocyanate with at least one active hydrogen-containing compound in the presence of the blowing agent composition described herein-above.

An isocyanate reactive composition can be prepared by blending at least one active hydrogen-containing compound with the blowing agent composition. Advantageously, the blend contains at least 1 and up to 50, preferably up to 25 weight percent of the blowing agent composition, based on the total weight of active hydrogen-containing compound and blowing agent composition.

Active hydrogen-containing compounds include those materials having two or more groups which contain an active hydrogen atom which reacts with an isocyanate. Preferred among such compounds are materials having at least two hydroxyl, primary or secondary amine, carboxylic acid, or thiol groups per molecule. Polyols, i.e., compounds having at least two hydroxyl groups per molecule, are especially preferred due to their desirable reactivity with polyisocyanates.

Additional examples of suitable active hydrogen containing compounds can be found in U.S. Pat. No. 6,590,005, incorporated herein by reference. For example, suitable polyester polyols include those prepared by reacting a carboxylic acid and/or a derivative thereof or a polycarboxylic anhydride with a polyhydric alcohol. The polycarboxylic acids may be any of the known aliphatic, cycloaliphatic, aromatic, and/or heterocyclic polycarboxylic acids and may be substituted, (e.g., with halogen atoms) and/or unsaturated. Examples of suitable polycarboxylic acids and anhydrides include oxalic acid, malonic acid, glutaric acid, pimelic acid, succinic acid, adipic acid, suberic acid, azelaic acid, sebacic acid, phthalic acid, isophthalic acid, terephthalic acid, trimellitic acid, trimellitic acid anhydride, pyromellitic dianhydride, phthalic acid anhydride, tetrahydrophthalic acid anhydride, hexahydrophthalic acid anhydride, endomethylene tetrahydrophthalic acid anhydride, glutaric acid anhydride acid, maleic acid, maleic acid anhydride, fumaric acid, and dimeric and trimeric fatty acids, such as those of oleic acid which may be in admixture with monomeric fatty acids. Simple esters of polycarboxylic acids may also be used such as terephthalic acid dimethylester, terephthalic acid bisglycol and extracts thereof. The polyhydric alcohols suitable for the preparation of polyester polyols may be aliphatic, cycloaliphatic, aromatic, and/or heterocyclic. The polyhydric alcohols optionally may include substituents which are inert in the reaction, for example, chlorine and bromine substituents, and/or may be unsaturated. Suitable amino alcohols, such as monoethanolamine, diethanolamine or the like may also be used. Examples of suitable polyhydric alcohols include ethylene glycol, propylene glycol, polyoxyalkylene glycols (such as diethylene glycol, polyethylene glycol, dipropylene glycol and polypropylene glycol), glycerol and trimethylolpropane.

Suitable additional isocyanate-reactive materials include polyether polyols, polyester polyols, polyhydroxy-terminated acetal resins, hydroxyl-terminated amines and polyamines, and the like. These additional isocyanate-reactive materials include hydrogen terminated polythioethers, polyamides, polyester amides, polycarbonates, polyacetals, polyolefins, polysiloxanes, and polymer polyols.

Other polyols include alkylene oxide derivatives of Mannich condensates, and aminoalkylpiperazine-initiated polyethers as described in U.S. Pat. Nos. 4,704,410 and 4,704,411. The low hydroxyl number, high equivalent weight alkylene oxide adducts of carbohydrate initiators such as sucrose and sorbitol may also be used.

In the process of making a polyisocyanate-based foam, the polyol(s), polyisocyanate and other components are contacted, thoroughly mixed and permitted to expand and cure into a cellular polymer. The particular mixing apparatus is not critical, and various types of mixing head and spray apparatus are conveniently used. It is often convenient, but not necessary, to preblend certain of the raw materials prior to reacting the polyisocyanate and active hydrogen-containing components. For example, it is often useful to blend the polyol(s), blowing agent, surfactant(s), catalyst(s) and other components except for polyisocyanates, and then contact this mixture with the polyisocyanate. Alternatively, all the components may be introduced individually to the mixing zone where the polyisocyanate and polyol(s) are contacted. It is also possible to pre-react all or a portion of the polyol(s) with the polyisocyanate to form a prepolymer.

The quantity of blowing agent composition employed when preparing a foam is sufficient to give a desired density to the foam. Advantageously, sufficient blowing agent is employed to provide a polyurethane foam having an overall density of from about 10 to about 500, preferably from about 18 to about 100 kg/m$^3$ (1 kg/m$^3$=0.062 lb./ft.$^3$).

It is often convenient to preblend the blowing agent composition with the active hydrogen-containing compound before contacting the resulting blend with the polyisocyanate. It is also possible to simultaneously blend together the polyisocyanate, active hydrogen-containing compound and blowing agent composition in one operation resulting in the production of polyisocyanate-based foam. Preferably the blowing agent composition is blended with the active hydrogen-containing compound before contacting with the polyisocyanate.

One aspect is for a rigid, closed-celled polyisocyanate-based foam. It is prepared by contacting an organic polyisocyanate with an active hydrogen-containing compound in the presence of the blowing agent composition characterized in that the so-prepared foam contains within its cells gaseous blowing agents.

The rigid closed-cell celled polyisocyanate-based foams are useful in spray insulation, as foam-in-place appliance foams, rigid insulating board stock, or in laminates.

In addition, according to certain embodiments, the blowing agents are used to blow thermoplastic foams, such as polystyrene, polyethylene foams, including low-density polyethylene foams, or polypropylene foams. Any of a wide range of conventional methods for blowing such thermoplastic foams can be adapted for use herein.

Another embodiment provides a foamable composition comprising thermoplastic foams, such as polystyrene, polyethylene (PE), preferably low density PE, or polypropylene (PP).

The thermoplastic foam bodies are conveniently produced by using conventional equipment comprising an extruder and associated means for (1) melting the resin; (2) homogeneously blending the blowing agent composition with the melt to form a plasticized mass at nonfoaming temperatures and pressures; (3) passing the plasticized mass at a controlled rate, temperature and pressure through a die having a desired shape, e.g., slit die for producing rectangular slabs of foam board having desired thickness and surface area, into an expansion zone; (4) allowing the extrudate to foam in the expansion zone maintainable at suitable temperatures and low pressures; (5) maintaining the expanding extrudate under such temperatures and pressures for a time sufficient for the viscosity of the extrudate to increase such that the cell size and density of the foam remain substantially unchanged and substantially free of ruptured cells at ambient temperature; e.g., 25° C. and atmospheric pressure; and (6) recovering the extruded foam body.

When preparing foams, it is often desirable to add a nucleating agent or other additives into the resin. Nucleating agents serve primarily to increase cell count and decrease cell size in the foam, and may be used in an amount of about 0.1 to about 10 parts by weight per 100 parts by weight of the resin. Typical nucleating agents comprise at lease one member selected from the group consisting of talc, sodium bicarbonate-citric acid mixtures, calcium silicate, carbon dioxide, among others.

In one aspect, the foaming amount of the blowing agent is in the range of from about 1 to about 30 weight percent based on the total weight of the resin plus blowing agent mixture, typically about 2 to 20 weight percent, and normally about 2 to about 10 weight percent. The lower the concentration of blowing agent, the greater the density of the resulting foam. The proper amount of blowing agent or resultant characteristics of the foam for any desired end-use is readily determined by a skilled person in this art. The resin is melted at a temperature of about 200 to about 235° C. depending upon the grade employed, and at nonfoaming pressures of about 600 psig or higher. The plasticized resin-blowing agent mixture is cooled under nonfoaming pressure to a temperature of about 115 to 150° C., normally 130° C., and extruded into the expansion zone at or below ambient temperature and at or below atmospheric pressure.

Representative foamed products that can be made in accordance with the present disclosure include, for example: (1) polystyrene foam sheet for the production of disposable thermoformed packaging materials; e.g., as disclosed in York, U.S. Pat. No. 5,204,169; (2) extruded polystyrene foam boards for use as residential and industrial sheathing and roofing materials, which may be from about 0.5 to 6 inches (1.25 to 15 cm) thick, up to 4 feet (122 cm) wide, with cross-sectional areas of from 0.17 to 3 square feet (0.016 to 0.28 square meter), and up to 27 feet (813 meters) long, with densities of from about 1.5 to 10 pounds per cubic foot (pcf) (25 to 160 kilograms per cubic meter (kg/m$^3$); (3) expandable foams in the form of large billets which may be up to about 2 feet (61 cm) thick, often at least 1.5 feet 46 cm) thick, up to 4 feet (1.22 meters) wide, up to 16 feet (4.8 meters) long, having a cross-sectional area of about 2 to 8 square feet (0.19 to 0.74 square meter) and a density of from 6 to 15 pcf (96 to 240 kg/m$^3$). Such foamed products are more fully described by Stockdopole and Welsh in the Encyclopedia of Polymer Science and Engineering, vol. 16, pages 193-205, John Wiley & Sons, 1989; hereby incorporated by reference.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit, and scope of the present disclosure. More specifically, it will be apparent that certain agents which are chemically related may be substituted for the agents described herein while the same or similar results would be achieved. All such similar substitutes and modifications apparent to those skilled in the art are deemed to be within the spirit, scope, and concept of the present disclosure as defined by the appended claims.

EXAMPLES

The present disclosure is further defined in the following Examples. It should be understood that these Examples, while indicating preferred embodiments, are given by way of illustration only. From the above discussion and these Examples, one skilled in the art can ascertain the preferred features, and without departing from the spirit and scope thereof, can make various changes and modifications to adapt it to various uses and conditions.

Example 1

Synthesis of 1,1,1,4,4,5,5,6,6,7,7,7-dodecafluorohept-2-ene (F14E)

Synthesis of $C_4F_9CH_2CHICF_3$
Perfluoro-n-butyliodide (180.1 gm, 0.52 moles) and 3,3,3-trifluoropropene (25.0 gm, 0.26 moles) were added to a 400 ml Hastelloy™ shaker tube and heated to 200° C. for 8 hours under autogenous pressure, which increased to a maximum of 428 PSI. The product was collected at room temperature. The above reaction was carried out again at these conditions and the products combined. It was then repeated doubling the amount of perfluoro-n-butyliodide and 3,3,3-trifluoropropene in the same 400 ml reactor. In this case the pressure increased to 573 PSI. The products of the three reactions were combined and distilled to give 322.4 gm of $C_4F_9CH_2CHICF_3$ (52.2°/35 mm) in 70% yield.
Conversion of $C_4F_9CH_2CHICF_3$ to F14E
$C_4F_9CH_2CHICF_3$ (322.4 gm, 0.73 moles) was added dropwise via addition funnel to a 2L round bottom flask equipped with stir a bar and connected to a packed distillation column and still head. The flask contained isopropyl alcohol (95 ml), KOH (303.7 gm, 0.54 moles) and water (303 ml). Product was collected, washed with sodium metabisulfite, water, dried with MgSO$_4$ and distilled through a 6" column filled with glass helices. The product, F14E (173.4 gm, 76%) boils at 78.2° C. It was characterized by $^{19}$F NMR (δ −66.7 (CF$_3$, m, 3F), −81.7(CF$_3$, m 3F), −124.8 (CF$_2$, m, 2F), −126.4 (CF$_2$, m, 2F), and −114.9 ppm (CF$_2$, m, 2F)) $^1$H NMR(δ 6.45) in chloroform-d solution.

Example 2

Synthesis of 1,1,1,2,2,5,5,6,6,7,7,8,8,8-tetradecafluorooct-3-ene (F24E)

Synthesis of $C_4F_9CHICH_2C_2F_5$
Perfluoroethyliodide (220 gm, 0.895 mole) and 3,3,4,4,5,5,6,6,6-nonafluorohex-1-ene (123 gm, 0.50 mole) were added to a 400 ml Hastelloy™ shaker tube and heated to 200° C. for 10 hours under autogenous pressure. The product from this and two others carried out under similar conditions were combined and washed with two 200 mL portions of 10 wt % aqueous sodium bisulfite. The organic phase was dried over calcium chloride and then distilled to give 277.4 gm of $C_4F_9CH_2CHICF_3$ (79-81° C./67-68 mm Hg) in 37% yield.
Conversion of $C_4F_9CHICH_2C_2F_5$ to F24E
A 1 L round bottom flask equipped with a mechanical stirrer, addition funnel, condenser, and thermocouple was charged with $C_4F_9CHICH_2C_2F_5$ (277.4 gm, 0.56 moles) and isopropanol (217.8 g). The addition funnel was charged with a solution of potassium hydroxide (74.5 g, 1.13 moles) dissolved in 83.8 g of water. The KOH solution was added dropwise to the flask with rapid stirring over the course of about one hour as the temperature slowly increased from 21° C. to 42° C. The reaction mass was diluted with water and the product recovered by phase separation. The product was washed with 50 mL portions of 10 wt % aqueous sodium bisulfite and water, dried over calcium chloride, and then distilled at atmospheric pressure. The product, F24E (128.7 gm, 63%) boils at 95.5° C. It was characterized by $^{19}$F NMR (δ −81.6 (CF$_3$, m, 3F), −85.4(CF$_3$, m 3F), −114.7 (CF$_2$, m, 2F), −118.1 (CF$_2$, m, 2F), −124.8 ppm (CF$_2$, m, 2F), −126.3 ppm (CF$_2$, m, 2F)) and $^1$H NMR (δ6.48) in chloroform-d solution.

Example 3

Synthesis of $CF_3CH=CHCF(CF_3)_2$

Synthesis of $CF_3CHICH_2CF(CF_3)_2$
(CF$_3$)$_2$CFI (265 gm, 0.9 moles) and 3,3,3-trifluoropropene (44.0 gm, 0.45 moles) were added to a 400 ml Hastelloy shaker tube and heated to 200° C. for 8 hours under autogenous pressure, which increased to a maximum of 585 psi. The product was collected at room temperature to give 110 gm of (CF$_3$)$_2$CFCH$_2$CHICF$_3$ (76-77° C./200 mm) in 62% yield.
Conversion of (CF$_3$)$_2$CFCH$_2$CHICF$_3$ to F131E
(CF$_3$)$_2$CFCH$_2$CHICF$_3$ (109 gm, 0.28 moles) was slowly added dropwise via addition funnel to a 500 ml round bottom flask heated to 42° C. equipped with stir a bar and connected to a short path distillation column and dry ice trap. The flask contained isopropyl alcohol (50 ml), KOH (109 gm, 1.96 moles) and water (109 ml). During the addition, the temperature increased from 42 to 55° C. After refluxing for 30 minutes, the temperature in the flask increased to 62° C. Product was collected, washed with water, dried with MgSO$_4$ and distilled. The product, F131E (41 gm, 55%), boils at 48-50°

C. and was characterized by 19F NMR (δ −187.6 (CF, m 1F), −77.1 (CF3, m 6F), −66.3 (CF3, m 3F) in chloroform-d solution.

Polyisocyanate-Based Foam Examples

To demonstrate effectiveness of unsaturated fluorocarbon blowing agents, polyurethane and polyisocyanurate foam samples were prepared by hand-mixing, using the two basic polyurethane foam formulations described in Example 4 and Example 5 below. The blowing agents may be generally premixed with the polyol or B-side for convenience. Foams may be prepared either as free-rise or molded samples. For free-rise foams, the reaction mixture is poured into an open, round cardboard container. For molded foams, the reaction mixture is poured into a 2½"×13"×15" (6.35 cm×30.02 cm×38.1 cm) heated aluminum mold.

Example 4

Polyisocyanurate Foam

| Component | Parts by Weight |
|---|---|
| aromatic polyester polyol (Stepanpol ® PS-2502A) | 120 |
| polysiloxane surfactant (Dabco DC-193) | 1.8 |
| potassium octanoate catalyst (Hexcem 977) | 3.2 |
| Tris-2,4,6-(dimethylaminomethyl)phenol/Bis(dimethylaminomethyl) phenol catalyst (Dabco TMR 30) | 0.4 |
| 1,1,1,4,4,5,5,5,Octafluooro-2-pentene (HFC-1438mzz) (Blowing Agent) | 80 |
| polymethylene polyphenylisocyanate isocyanate (Papi ® 580) | 190 |

All components except the isocyanate were premixed as a B-side. The isocyanate (A-side) was then added and mixed with a mechanical stirrer for 10 seconds. The foam reaction mixture was poured into a closed aluminum mold warmed to about 100° F. and allowed to expand. When cured, a 1"×1"×12" sample was cut from the core of the molded foam.

The core sample was about 2.2 pounds/ft$^3$ (PCF) (35.2 kg/m$^3$) density, had an exceptionally fine cell structure, and remained dimensionally stable. Magnified photographs of the foam showed a uniform, highly closed cell structure and cell sizes about 200-300 microns (μ). Using a LaserComp FOX 304 Thermal Conductivity Meter, initial insulation value (R-value) was measured at 7.4/inch (thermal conductivity of 19.5 milliW/(mK) at a mean temperature of 24.0° C. or 0.135 BTU-in/hr-ft$^2$-° F. at a mean temperature of 75.2° F.).

Example 5

Polyurethane Pour-in-Place Foam

| Component | Parts by Weight |
|---|---|
| sucrose/glycerine initiated polyether polyol (Voranol ® 360) | 140 |
| silicone surfactant (Witco L-6900) | 3.0 |
| N,N-Dimethylcyclohexylamine catalyst (Polycat 8) | 1.7 |
| pentamethyldiethylenetriamine catalyst (Polycat 5) | 0.4 |
| 2-Methyl(n-methyl amino b-sodium acetate nonyl phenol) catalyst (Curithane ® 52) | 0.5 |
| Water | 2.1 |
| Blowing Agent 1,1,1,4,4,5,5,5,Octafluooro-2-pentene (HFC-1438mzz) | 70 |
| polymethylene polyphenylisocyanate isocyanate (Papi ® 27) | 169 |

All components except the isocyanate were premixed as a B-side. The isocyanate (A-side) was then added and mixed with a mechanical stirrer for 10 seconds. The foam reaction mixture was poured into a closed aluminum mold warmed to about 100° F. and allowed to expand. When cured, a 1"×1"×12" sample was cut from the core of the molded foam.

The core sample was about 2.0 pounds/ft$^3$ (PCF) (32.0 kg/m$^3$) density, had a good cell structure though it did contain some voids, and remained dimensionally stable. Magnified photographs of the foam showed a uniform, highly closed cell structure, excluding the voids, and cell sizes about 200-300 microns (μ). Using a LaserComp FOX 304 Thermal Conductivity Meter, initial insulation value was measured at 4.9/inch (29.5 milliW/(mK) at a mean temperature of 24.0° C. or thermal conductivity of 0.2044 BTU-in/hr-ft$^2$-° F. at a mean temperature of 75.2° F.),

Example 6

Polyisocyanurate Foam

| Component | Parts by Weight |
|---|---|
| aromatic polyester polyol (Stepanpol ® PS-2502A) | 14.4 |
| polysiloxane surfactant (Dabco DC-193) | 0.42 |
| Potassium octanoate catalyst (Hexcem 977) | 0.8 |
| Tris-2,4,6-(dimethylaminomethyl)phenol/Bis(dimethylaminomethyl)phenol catalyst (Dabco TMR 30) | 0.15 |
| 1,1,1,4,4,4 Hexafluooro-2-butene (HFC-1336mzz, Z-isomer) (Blowing Agent) | 12.0 |
| polymethylene polyphenylisocyanate isocyanate (Papi ® 580) | 22.8 |

All components except the isocyanate were premixed as a B-side. The isocyanate (A-side) was then added and hand-mixed for about 30 seconds. The foam reaction mixture was allowed to rise in the beaker. The blowing agent mixed well with the B-side and foamed the polymer. Foam density was initially high because the catalyst amounts and ratio were not optimal for the HFC-1336mzz boiling point, and the amounts of catalyst were adjusted to decrease density.

Example 7

Blowing Agent Solubility Effect on Foam Cell Structure

These unsaturated fluorocarbons offer an advantage of improved foam cell structure because their solubility is different than other typically used blowing agents. Their reduced solubility in the B-side requires proper mixing, but once mixed, they demonstrate a good affinity for the B-side, and being somewhat insoluble, act to help seed small cell growth during the foaming reaction.

This was observed in preparing the foam examples 4 and 5, above. In the case of example 4, the blowing agent (HFC-1438mzz) was mixed in the B-side until a mousse-like consistency was obtained. At that point, the blowing agent was well dispersed in the B-side, with no loss upon sitting at room temperature. When this B-side mixture was foamed, it resulted in the exceptionally fine cell structure described above, and contributed to the high R-value.

In example 5, the blowing agent was not mixed as thoroughly in the B-side. In this case, voids were observed in the foam, but the cell structure excluding the voids remained small and consistent. The resultant insulation value was acceptable despite the voids, demonstrating that these unsaturated fluorocarbons can improve cell structure and foam properties such as to overcome potential processing difficulties that otherwise would detrimentally impact foam performance.

Thermoplastic Foam Examples

Example 8

The following example serves to illustrate the ability to use unsaturated fluorocarbon blowing agents to produce thermoplastic foam insulation, specifically a polystyrene insulation foam, with fine, uniform cell structure, long-term insulation value, and good dimensional stability.

To produce polystyrene foam insulation board, a commercial tandem extruder equipped with die, designed for insulation board foam, is used. Such a configuration employs a primary extruder and a secondary extruder, with a slit die. A typical polystyrene resin would be Shell NX600 general purpose, 2.5 melt index, and a typical nucleator would be magnesium silicate talc.

TABLE 4

| Typical Extruder Operating Parameters | |
|---|---|
| Primary extruder (rpm) | 70 |
| Extrusion rate (kg/hr) | 430 |
| Blowing agent rate (kg/hr) | 46.5 |
| Blowing agent concentration (wt %) | 10.8 |
| Nucleator concentration (wt %) | 0.6 |
| Secondary extruder speed (rpm) | 4.9 |
| Die pressure (psig) | 1484 |
| Melt temperature (° C.) | 129 |

TABLE 4-continued

| Typical Extruder Operating Parameters | |
|---|---|
| Die gap (mm) | 1.9 |
| Die width (mm) | 100 |
| Foam thickness (mm) | 52 |
| Foam width (mm) | 317 |
| Foam density (kg/m$^3$) | 30.5 |

Example 9

In this example, polystyrene foam sheet is prepared using unsaturated fluorocarbons as the blowing agent. The polystyrene foam sheet is ultimately thermoformed into food service packaging, like egg cartons, hamburger cartons, meat trays, plates, etc.

Foam sheet is produced using a conventional tandem extrusion system. Foam is extruded through an annular die, stretched over a mandrel about 4 times the die's diameter, and slit to produce a single sheet.

A typical formulation is:
88 to 97 wt. percent polystyrene resin
2 to 8 wt. percent unsaturated fluorocarbon blowing agent
1 to 4 wt. percent nucleating agent The polystyrene sheet is typically extruded to a thickness of 50 to 300 mils and at a rate of approximately 1,000 pounds of plastic per hour. Typical extruder conditions range from 1,000 to 4,000 psi (70.3 kg/cm to 281.3 kg/cm) and 200° F. to 400° F. (93.3° C. to 204.4° C.). The blowing agent concentration in the feed material will change depending on the desired thickness (thicker product requires more blowing agent). Once the polystyrene has been extruded, it is typically aged between 3 days to 2 weeks. During this time, it is stored in rolls in a warehouse. Some blowing agent permeates out of the foam at this time, but at a relatively slow rate.

After storage, the rolls of foam are thermoformed, producing the desired type of end-product (e.g., clam-shell containers, plates, etc.).

Example 10

Experiments were conducted to assess the stability of HFC-1225ye for thermoplastic foams. 1,2,3,3,3-pentafluoro-1-propene (HFC-1225ye), 1,1-difluoroethane (HFC-152a) and 1,1,1,2-tetrafluoroethane (HFC-134a) were all analyzed by GC/MS prior to the testing and were found to be 100% pure. Polystyrene, talc nucleator, a 1010 Mild Steel Coupon, and air was heated to 260° C. in a pressure vessel with blowing agent and held 24 hours. After 24 hours, the vessel was cooled and all gaseous products were collected from the vessel for analysis.

| GC/MS Analysis of Gases after Exposure to 260° C. for 24 Hours | | | | | | | | | | | |
|---|---|---|---|---|---|---|---|---|---|---|---|
| | \multicolumn{11}{c}{Sample Number} | | | | | | | | | | |
| | 24a | 24b | 24c | 32b | 39c | 32a | 39b | 39d | 22 | 24d | 39a |
| | \multicolumn{11}{c}{Composition in Wt %:} | | | | | | | | | | |
| Polystyrene Mistron Vapor | 90 | 90 | 87 | 87 | 87 | 87 | 87 | 87 | 87 | 87 | 87 |
| Magnesium Silicate Talc | | | 3 | 3 | 3 | 3 | 3 | 3 | | | |
| Safoam ® FPN3 (sodium salts of carbonic & polycarboxylic acids) | | | | | | | | | 3 | 3 | 3 |
| HFC-1225ye | 10 | 10 | 10 | 10 | 10 | | | | 10 | 10 | 10 |
| HFC-152a | | | | | | 10 | 10 | | | | |

-continued

GC/MS Analysis of Gases after Exposure to 260° C. for 24 Hours

| | \multicolumn{11}{c}{Sample Number} | | | | | | | | | | |
|---|---|---|---|---|---|---|---|---|---|---|---|
| | 24a | 24b | 24c | 32b | 39c | 32a | 39b | 39d | 22 | 24d | 39a |
| | | | | | Composition in Wt %: | | | | | | |
| HFC-134a | | | | | | | | 10 | | | |
| 1010 Mild Steel Coupon | x | x | x | x | x | x | x | x | x | x | X |
| Air | X | x | x | x | x | x | x | x | x | x | X |
| Blowing Agent Purity after Exposure | | >99.9% | | | | 93.4% | 96.7% | 100% | | >99.9% | |

The test data show that HFC-1225ye was surprisingly as stable as HFC-134a and more stable than HFC-152a under extrusion conditions.

The steel coupons from runs 32a, 32b and 24d were analyzed by Electron Spectroscopy for Chemical Analysis (ESCA). Fluoride ions (F$^-$) were observed on the surface of all coupons. Estimated concentrations of fluoride ion are shown in the table below.

ESCA Analysis Results (Unit: Atom %)

| Sample Number | Blowing Agents | Talc | Fluoride ion (atom %) |
|---|---|---|---|
| 32a | HFC-152a | Mistron | 15 |
| 32b | HFC-1225ye | Mistron | 0.3 |
| 24d | HFC-1225ye | Safoam | 0.2 |
| 39d | HFC-1225ye | Mistron | 0.3 |

Example 11

Experiments were conducted to assess the compatibility of the unsaturated fluorocarbons for thermoplastic foams. Polystyrene and talc nucleator were heated to 260° C. in a pressure vessel with blowing agent and held 24 hours. After 24 hours, the vessel was cooled and a polystyrene sample recovered for thermal gravimetric analysis (TGA). Weight loss versus temperature was compared for the polystyrene samples heated with blowing agents to a control sample of starting polystyrene material. The TGA analysis shows that blowing agent was admixed in the melt and the weight loss provides an approximation of the amount of blowing agent that mixed in the melt. The data indicates improved solubility for the unsaturated fluorocarbon blowing agent versus current HFC products.

| # | Sample | Blowing Agent | Weight Loss @ 300° C. |
|---|---|---|---|
| — | Polystyrene Control | None | 0.7% |
| 24a | Polystyrene | 1,2,3,3,3-pentafluoro-1-propene | 4.26% |
| 24b | Polystyrene | 1,2,3,3,3-pentafluoro-1-propene | 2.5% |
| 39c | Polystyrene + Talc | 1,2,3,3,3-pentafluoro-1-propene | 5.38% |
| 39b | Polystyrene + Talc | HFC-152a | 2.44% |
| 39d | Polystyrene + Talc | HFC-134a | 3.99% |
| 39a | Polystyrene + Safoam | 1,2,3,3,3-pentafluoro-1-propene | 4.79% |

We claim:

1. A method of forming a polyisocyanate-based foam comprising
   forming a blend by mixing a blowing agent comprising a hydrofluorocarbon, with
   at least one polyol, wherein said blowing agent is not fully soluble in said polyol
   reacting at least one organic polyisocyanate with said blend, wherein said blowing agent comprising a hydrofluorocarbon having the formula E- or Z—R1CH=CHR2, wherein R1 and R2 are, independently, C1 to C6 perfluoroalkyl groups.

2. The method of claim 1, wherein said blend contains at least 5 to 50 wt. % blowing agent, based on the total weight of active hydrogen-containing compound and blowing agent.

3. The method of claim 2, wherein said blend contains at least 5 to 25 wt. % blowing agent, based on the total weight of polyol and blowing agent.

4. A method of producing polyurethane foams, comprising the steps of blending at least one polyol and at least one blowing agent, to form B side mixture having the appearance of an emulsion, said blowing agent comprising a hydrofluorocarbons selected from the group consisting of E-CF3CH=CHCF3, Z—CF3CH=CHCF3, E-CF3CH=CHCF2CF3, and Z—CF3CH=CHCF2CF3, and reacting said B side mixture with an A side mixture, said A side mixture comprising at least one organic polyisocyanate.

5. The method of claim 4, wherein the at least one organic polyisocyanate, the at least one polyol and the blowing agent of claim 1 are blended simultaneously.

6. The method of claim 5, wherein the reacting step is performed in the presence of at least one catalyst.

7. The method of claim 5, wherein the B side further comprises at least one auxiliary component, said auxiliary component selected from the group consisting of a surfactant, a flame retardant, a preservative, a colorant, an antioxidant, a reinforcing agent, a filler, an antistatic agent, or a combination thereof.

8. The method of claim 7, wherein the at least auxiliary component is a surfactant present in a range of from about 0.2 to about 5 parts surfactant per 100 parts by weight polyol.

9. The method of claim 8, wherein said surfactant is a liquid or solid organosilicone compound, a polyethylene glycol ether of a long chain alcohol, a tertiary amine or alkanolamine salt of a long chain alkyl acid sulfate ester, an alkyl sulfonic ester, or an alkyl arylsulfonic acid.

10. The method of claim 6, wherein the at least one catalyst is present in a range of from about 0.1 to about 5 parts catalyst per 100 parts by weight of polyol.

11. The method of claim 1 wherein said at least one polyol is a polyester polyol.

12. The method of claim 11 wherein said at least on polyol is prepared by reacting a carboxylic acid with a polyhydric alcohol.

13. The method of claim 11 wherein said at least on polyol is prepared by reacting a carboxylic acid with a polyhydric alcohol.

14. The method of claim 1, wherein the blowing agent is thoroughly mixed with the polyol.

* * * * *